United States Patent
Kamatani et al.

(10) Patent No.: US 8,017,774 B2
(45) Date of Patent: Sep. 13, 2011

(54) PRODUCING METHOD FOR IRIDIUM COMPLEX

(75) Inventors: Jun Kamatani, Tokyo (JP); Shinjiro Okada, Kamakura (JP); Takao Takiguchi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 551 days.

(21) Appl. No.: 11/686,441

(22) Filed: Mar. 15, 2007

(65) Prior Publication Data

US 2007/0232803 A1 Oct. 4, 2007

(30) Foreign Application Priority Data

Mar. 31, 2006 (JP) .................................. 2006-099892

(51) Int. Cl.
  *C07F 15/00* (2006.01)
(52) U.S. Cl. ............. 546/2; 548/101; 556/136; 556/137
(58) Field of Classification Search ........ 546/2; 548/101; 556/136, 137
See application file for complete search history.

(56) References Cited

U.S. PATENT DOCUMENTS

| | | | | |
|---|---|---|---|---|
| 6,733,905 B2 | 5/2004 | Takiguchi et al. | ............ | 428/690 |
| 6,797,980 B2 | 9/2004 | Takiguchi et al. | ............ | 257/40 |
| 7,108,924 B2 | 9/2006 | Kamatani et al. | ............ | 428/690 |
| 7,166,958 B2 | 1/2007 | Furugori et al. | ............ | 313/504 |
| 7,189,466 B2 | 3/2007 | Moriyama et al. | ............ | 428/690 |
| 7,238,435 B2 | 7/2007 | Kamatani et al. | ............ | 428/690 |
| 2002/0064681 A1 | 5/2002 | Takiguchi et al. | ............ | 428/690 |
| 2002/0094453 A1 | 7/2002 | Takiguchi et al. | ............ | 428/690 |
| 2002/0100906 A1 | 8/2002 | Takiguchi et al. | ............ | 257/40 |
| 2003/0186080 A1 | 10/2003 | Kamatani et al. | ............ | 428/690 |
| 2003/0224208 A1 | 12/2003 | Kamatani et al. | ............ | 428/690 |
| 2004/0169461 A1 | 9/2004 | Moriyama et al. | ............ | 428/690 |
| 2005/0035707 A1 | 2/2005 | Furugori et al. | ............ | 313/504 |
| 2005/0196639 A1 | 9/2005 | Kamatani et al. | ............ | 428/690 |
| 2006/0003171 A1 | 1/2006 | Igawa et al. | ............ | 428/447 |
| 2006/0280968 A1 | 12/2006 | Kamatani et al. | ............ | 428/690 |

FOREIGN PATENT DOCUMENTS

| | | |
|---|---|---|
| EP | 1 191 613 A2 | 3/2002 |
| JP | 2001-345183 | 12/2001 |
| JP | 2001-345183 A | 12/2001 |
| JP | 2002-226495 | 8/2002 |
| JP | 2002-226495 A | 8/2002 |
| JP | 2002-234894 | 8/2002 |
| JP | 2002-234894 A | 8/2002 |
| JP | 2003-146996 | 5/2003 |
| JP | 2003-146996 A | 5/2003 |
| JP | 2005-170851 | 6/2005 |
| JP | 2005-170851 A | 6/2005 |

OTHER PUBLICATIONS

Dedeian et al. "A New Synthetic Route to the Preparation of a Series of Strong Photoreducing Agents: fac Tris-Ortho-Metalated Complexes of Iridium (III) with Substituted 2-Phenylpyridines" Inorganic Chemistry, 1991, vol. 30, 1685-1687.*
Pyo et al. "An organic electrophosphorescent device driven by all-organic thin-film transistor using photoacryl as a gate insulator" Current Applied Physics, 2002, vol. 2, pp. 417-419.*
Chen et al., "Recent Developments in Molecular Organic Electroluminescent Materials," *Macromol. Symp.*, vol. 125, 1-48 (1997).
Vincett et al., "Electrical Conduction and Low Voltage Blue Electroluminescence in Vacuum-deposited Organic Films," *Thin Solid Films*, vol. 94, 171-183 (1982).
Burroughes et al., "Light-emitting Diodes Based on Conjugated Polymers," *Nature*, vol. 347, 539-541 (1990).
O'Brien et al., "Improved Energy Transfer in Electrophosphorescent Devices," *App. Phys. Lett.*, vol. 74, No. 3, 442-444 (1999).
Baldo et al., "Very High-efficiency Green Organic Light-emitting Devices Based on Electrophosphorescence," *Appl. Phys. Lett.*, vol. 75, No. 1, 4-6 (1999).
Dedeian et al., "A New Synthetic Route to the Preparation of a Series of Strong Photoreducing Agents: *fac* Tris-Ortho-Metalated Complexes of Iridium (III) with Substituted 2-Phenylpyridines," *Inorg. Chem.*, vol. 30, 1685-1687 (1991).
Colombo et al., "Synthesis and High-Resolution Optical Spectroscopy of Bis (2-(2-thienyl)pyridinato-$C^3$,N') (2,2'-bipyridine)iridium (III)," *Inorg. Chem.*, vol. 32, 3081-3087 (1993).
Lamansky et al., "Synthesis and Characterization of Phosphorescent Cyclometalated Iridium Complexes," *Inorg. Chem.*, vol. 40, 1704-1711 (2001).

* cited by examiner

*Primary Examiner* — Joseph Kosack
(74) *Attorney, Agent, or Firm* — Fitzpatrick, Cella, Harper & Scinto

(57) ABSTRACT

The invention provides a method for producing an iridium complex with a high yield at a low temperature, and an organic electroluminescence device (organic EL device) having an light output high in efficiency and high luminance in a range from blue to red region. An iridium complex for the organic EL device is produced from an iridium complex having a 4-membered ring structure as an auxiliary ligand. The organic EL device is composed of at least a pair of electrodes serving as an anode and a cathode, and an organic compound layer interposed between the electrodes, and the organic compound layer contains an iridium complex represented by a following structure:

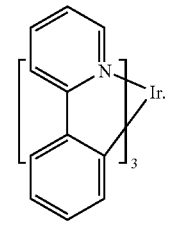

4 Claims, 3 Drawing Sheets

PRODUCING METHOD FOR IRIDIUM COMPLEX

BACKGROUND OF THE INVENTION

1. Field of the Invention

The present invention relates to a method for producing an iridium complex by the use of a novel intermediate. The iridium complex obtained by the producing method of the present invention can be utilized in an organic electroluminescence device and a display apparatus. More specifically, the method for producing an iridium complex of the present invention uses an auxiliary ligand having an unstable 4-membered ring structure as an intermediate, thereby enabling reaction to proceed at a low temperature to produce an iridium complex with a high yield.

2. Description of the Related Art

With organic light emission devices, an example in an early reference is known in which a voltage is applied to an evaporated anthracene film to cause a light emission (Thin Solid Films, 94 (1982) 171: non-patent reference 1). In recent years, the organic light emission devices have been found to have advantages such as the easiness of larger area formation in comparison with inorganic light emission devices, a possibility of obtaining desired light emission color due to the development of various new materials and a drivability at a low voltage, and is now actively developed for realizing light emission devices fast in response and high in efficiency, including the development of materials.

The organic electroluminescence (EL) device generally has a structure in which a pair of upper and lower electrode layers and an organic material layer interposed therebetween including a light emission layer are formed on a transparent substrate, as described in Macromol. Symp. 125, 1-48 (1997) (non-patent reference 2).

In addition to the conventional light emission utilizing fluorescence ascribable to a transition from a singlet exciton to a ground state, devices are recently investigated utilizing phosphorescent light emission through a triplet exciton, as typified by D. F. O'Brien et al., Improved energy transfer in electrophosphorescent device, Applied Physics Letters, Vol. 74, No. 3, p 422 (1999) (non-patent reference 3) and by M. A. Baldo et al., Very high-efficiency green organic light-emitting devices based on electrophosphorescence, Applied Physics Letters, Vol. 75, No. 1, p 4 (1999) (non-patent reference 4). These references principally utilize an organic layer of a 4-layered structure which is composed of, from the anode side, a hole transport layer, a light emission layer, an exciton diffusion preventing layer and an electron transport layer. The materials being used include a carrier transport material and a phosphorescent material $Ir(ppy)_3$ shown below.

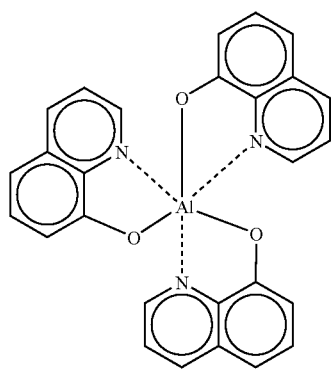

Alq3

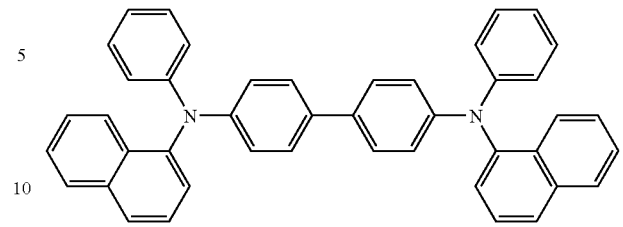

α-NPD

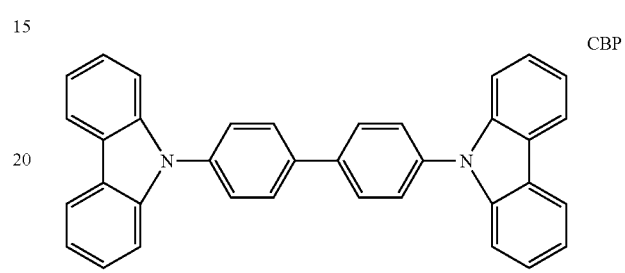

CBP

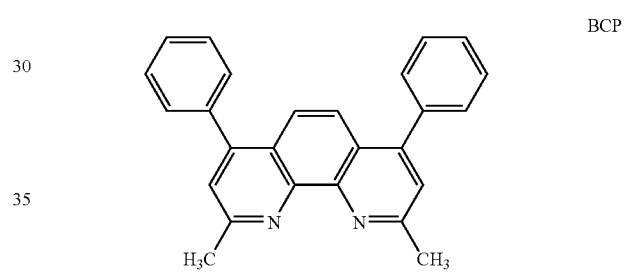

BCP

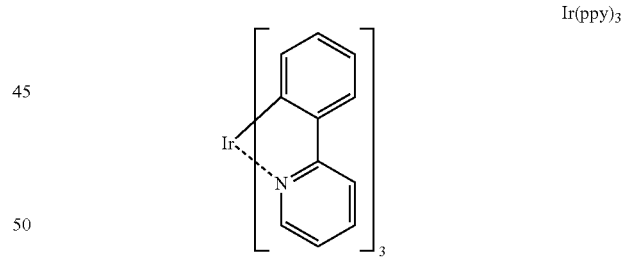

Ir(ppy)₃

Light emission from an ultraviolet region to an infrared region is possible by changing the types of fluorescent organic compounds, and various compounds are recently being actively investigated.

In addition to the organic light emission devices utilizing low-molecular materials as described above, an organic light emission device utilizing a conjugated polymer is reported by a group at Cambridge Univ. (Nature 347,539 (1990), non-patent reference 5). This report confirmed light emission from a single layer by forming a film of polyphenylenevinylene (PPV) by means of a coating system.

In this manner, the organic light emission devices are recently showing remarkable progress to make it possible to achieve a thin light-weight light emission device with features of a low applied voltage, a high luminance, a wide variety of light emission wavelengths, and a high-speed response, thus suggesting possibilities of wide applications.

However, under the present conditions, a light output higher in luminance and higher conversion efficiency are being sought. In addition, various problems remain unsolved concerning durability, such as changes over time during long-term service, and concerning deterioration due to oxygen-containing atmospheric gases or moisture. Also, at present, due to the fact that a temperature of about 200° C. is required at the time of production, productivity is not very high.

SUMMARY OF THE INVENTION

The present invention is characterized in synthesizing an iridium complex for an organic EL device by using as a raw material an iridium complex having a 4-membered ring structure for an auxiliary ligand. The present invention is to provide a method for producing an iridium complex at a low temperature with a high yield. When the compound obtained by the method for synthesizing an iridium complex of the present invention is used as a compound for an organic EL device, an organic EL device can be realized generating high-luminance light from blue to red with high efficiency.

More specifically, the present invention provides a method for producing an iridium complex by reacting a metal complex having a partial structure represented by a following general formula (1):

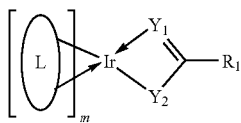

(1)

(wherein L represents a monovalent bidentate ligand having at least an aromatic ring or a heterocycle which may be substituted; $R_1$ is a group selected from the group consisting of a hydrogen atom, a halogen atom, a linear or branched alkyl group containing 1 to 20 carbon atoms (in which one or unadjacent two or more methylene groups may be replaced by at least one group selected from the group consisting of —O—, —S—, —CO—, —CO—O—, —O—CO—, —CH=CH— and —C≡C—, or one or two or more methylene groups may be replaced by an arylene group which may be substituted or by a divalent heterocyclic group which may be substituted, and one or two or more hydrogen atoms may be replaced by a fluorine atom), an amino group which may be substituted, a silyl group which may be substituted, a phenyl group which may be substituted, a naphthyl group, a pyrenyl group, a phenanthrenyl group, a chrysenyl group, a fluoranthenyl group, a triphenylenyl group and a heterocyclic group which may be substituted; and $Y_1$ and $Y_2$ are each independently a group selected from the group consisting of an oxygen atom, a sulfur atom, a selenium atom, and a nitrogen atom) with a compound represented by a following general formula (3):

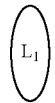

(3)

(wherein $L_1$ represents a monovalent bidentate ligand having at least one aromatic ring or one heterocycle which may be substituted), thereby producing an iridium complex represented by a following general formula (2):

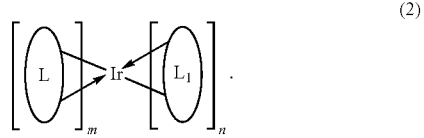

(2)

(wherein L and $L_1$ are as defined above; m represents an integer from 1 to 3 and n represents an integer from 0 to 2 in which m+n=3).

The present invention also provides a method for producing an iridium complex by reacting the metal complex having the partial structure represented by the general formula (1) with the ligand L to produce a compound represented by a following general formula (4):

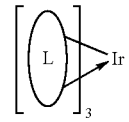

(4)

(wherein L represents a monovalent bidentate ligand having at least one aromatic ring or one heterocycle which may be substituted).

Specific examples of the aromatic ring in L and $L_1$ include a phenyl group, a naphthyl group, a fluorenyl group, an anthracenyl group, a fluoranthenyl group, and a pyrenyl group. Specific examples of the heterocycle include a thiernyl group, a pyridyl group, an imidazoyl group, an oxazoyl group, a quinolyl group, an isoquinolyl group, a pyrazyl group and a triazoyl group.

The iridium complex obtained by the producing method of the present invention is a phosphorescence emission material high in efficiency having light emission in a region from blue to red.

An organic EL device utilizing the iridium complex obtained by the producing method of the present invention, particularly an organic EL device utilizing the iridium complex as a light emission material in a light emission layer, has a light output high in efficiency, high luminance, and high durability.

The present invention can provide a method for producing an iridium complex with a high yield at a low temperature. Also, the present invention can provide an organic EL device having a light output high in efficiency and high luminance in a region from blue to red, using the iridium complex produced by such a producing method as a compound for the organic EL device. Furthermore, a display apparatus utilizing the organic EL device of the present invention can be provided.

Further measures of the present invention will become apparent from the following description of exemplary embodiments with reference to the attached drawings.

DESCRIPTION OF THE EMBODIMENTS

The present invention will be described in detail below, the present invention relates to a novel producing method for an iridium complex. The use of an auxiliary ligand having an unstable 4-membered ring structure as an intermediate enables a reaction at a low temperature, thus enabling a desired iridium complex to be obtained with a high yield.

Figure 1:
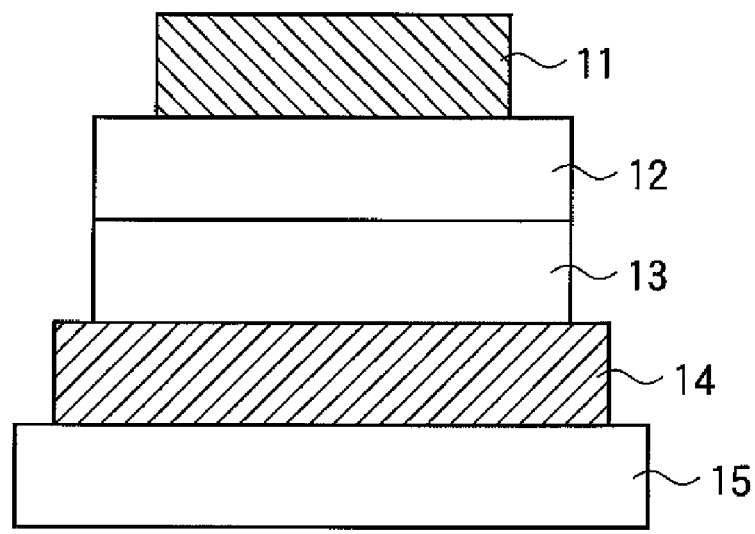
FIG. 1 is a view illustrating an example of the organic EL device of the present invention.
Figure 2:
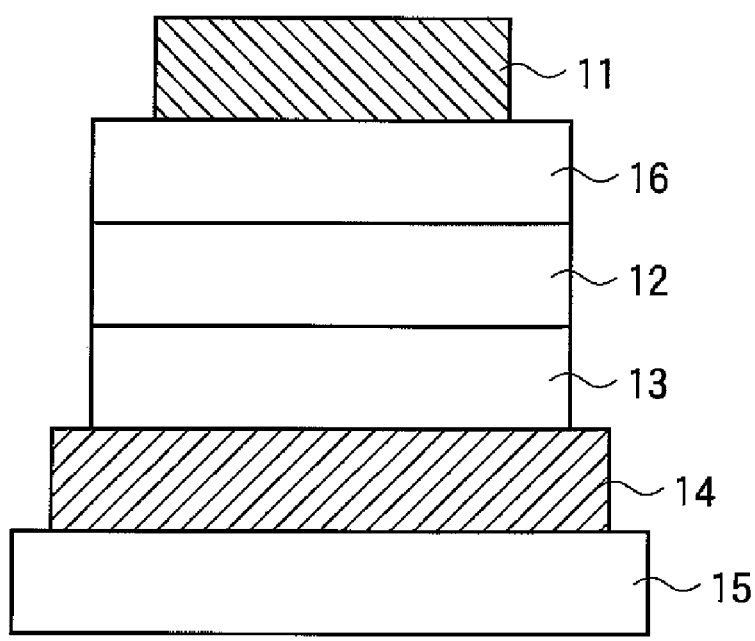
FIG. 2 is a view illustrating another example of the organic EL device of the present invention.
Figure 3:
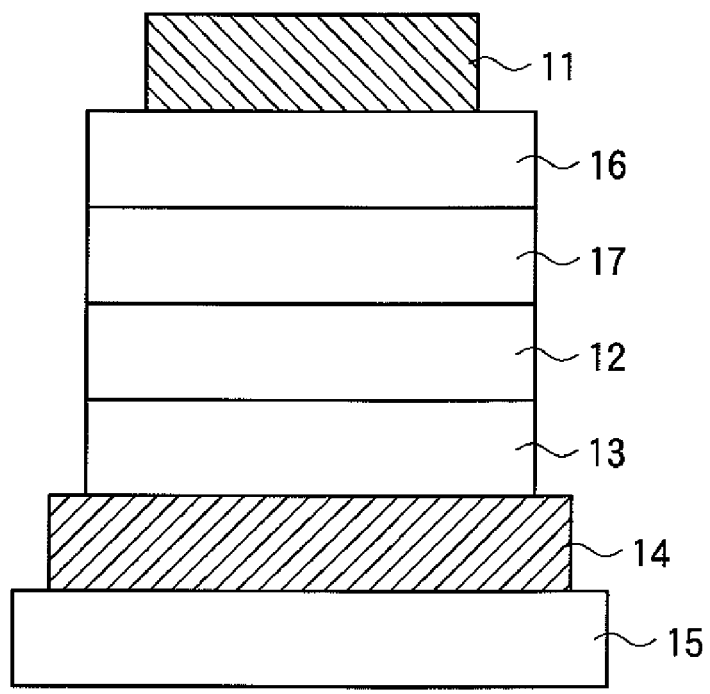
FIG. 3 is a view illustrating another example of the organic EL device of the present invention.

FIGS. 1 to 3 illustrate basic constructions of an organic EL device utilizing the iridium complex of the present invention. In these drawings, 11 denotes a metal electrode; 12, a light emission layer; 13, a hole transport layer; 14, a transparent electrode, 15, a transparent substrate; 16, an electron transport layer; and 17, an exciton diffusion preventing layer.

As illustrated in FIG. 1, an organic EL device generally include, on a transparent substrate 15, a transparent electrode 14 having a thickness of from 50 to 200 nm, an organic film layer comprised of plural layers, and a metal electrode 11 facing the transparent electrode through the organic film layer.

FIG. 1 illustrates an example in which the organic layer includes a light emission layer 12 and a hole transport layer 13. As the transparent electrode 14, ITO having a large work function is used to facilitate the hole injection from the transparent electrode 14 into the hole transport layer 13. As the metal electrode 11, a metal material having a small work function, such as aluminum, magnesium or an alloy thereof, is used to facilitate the electron injection into the organic layer.

The compound of the present invention is used for the light emission layer 12, and for the hole transport layer 13, it is possible to conveniently use an electron-donating material such as a triphenyldiamine derivative whose typical example is α-NPD of the following formula:

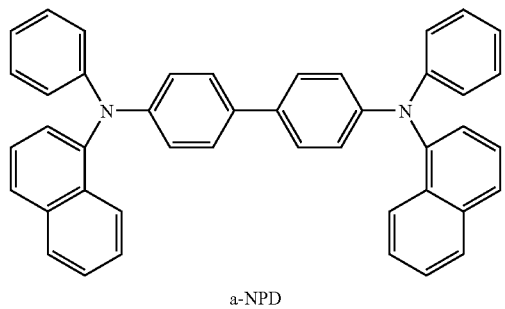

a-NPD

The device of the above-described structure exhibits rectifying properties, and when an electric field is applied in such a manner that the metal electrode 11 serves as a cathode and the transparent electrode 14 serves as an anode, electrons are injected from the metal electrode 11 into the light emission layer 12 while holes are injected from the transparent electrode 14.

The holes and electrons thus injected are recombined in the light emission layer 12 to generate excitons, thus generate light emission. In this case, the hole transport layer 13 serves as a blocking layer for the electrons to elevate the recombination efficiency at the interface between the light emission layer 12 and the hole transport layer 13, thereby elevating the light emission efficiency.

In the structure illustrated in FIG. 2, an electron transport layer 16 is further provided between the metal electrode 11 and the light emission layer 12 in FIG. 1. The light emitting function is thus separated from the functions of transporting electrons and holes to achieve a more effective carrier blocking construction, thereby improving the light emission efficiency. As the electron transport layer 16, an oxadiazole derivative may be used.

As illustrated in FIG. 3, it is also preferable to employ a 4-layered structure composed of, from the side of the transparent electrode 14 serving as the anode, a hole transport layer 13, a light emission layer 12, an exciton diffusion preventing layer 17, an electron transport layer 16, and the metal electrode 11.

The novel method for producing an iridium complex of the present invention to be used for such application, is characterized by the skeleton of an auxiliary ligand of a complex used as an intermediate. More specifically, it is characterized in that the bond between an auxiliary ligand and a metal is formed from a 4-membered ring structure, thereby producing an intermediate high in reactivity.

Prior methods for synthesizing an iridium complex include a one-step synthesis method using an iridium acetylacetonate complex as a raw material (Inorganic Chem., 1991, Vol. 30, 1685), an iridium complex synthesis method through a method of synthesizing a 2-nuclear complex (Inorganic Chem., 1993, Vol. 32, 3081), and a three-step synthesis through an acetylacetone compound forming a 6-membered ring with a light emitting ligand and a metal complex (Inorganic Chem., 2001, Vol. 40, 1704).

In the above methods, the temperature is elevated to about 200° C. to produce the iridium complex. In general, they are accompanied by side reaction. Also, in the case where the ligand has a low boiling point, such as a ligand containing a fluorine atom(s) or a ligand of a small molecular weight, it is expelled from the system, thus reaction efficiency is lowered to reduce the yield.

The present invention utilizes, as a raw material for synthesizing an iridium complex including three light-emitting ligands, an iridium complex having a light-emitting ligand, iridium and an auxiliary ligand forming a 4-membered ring. The coordination number of the auxiliary ligand with the metal complex is adopted to form a 4-membered ring structure, thus lowering the stability of the complex and enhancing the reactivity. Such an intermediate makes it possible to synthesize any one of an iridium complex having the same ligand, an iridium complex having a different ligand, an iridium complex having a facial structure, and an iridium complex having a meridional structure. This is particularly effective in the case of using as a ligand a compound that generates only a facial skeleton, such as a phenylisoquinoline skeleton, regardless of reaction temperature.

The stabilities of rings formed only from carbon-carbon bonds are lowered in the order of 6-membered ring>5-membered ring>4-membered ring. In the present invention, the conditions may be somewhat different because the Ir metal intervenes, but a 4-membered ring is more unstable in comparison with a 5- or 6-membered ring and can improve the reactivity.

In consideration of these points, a raw material having a 4-membered ring structure is more suitable for synthesizing the desired light-emitting iridium complex. The auxiliary ligand forming a 4-membered ring structure can be prepared from acetic acid as the raw material to provide a very inexpensive auxiliary ligand, thereby reducing the cost of production. Such an iridium complex having the ligand of a 4-membered ring structure may also be utilized as a material for a light emission device and has an example of being used with a light emission material, but, in the present invention, is principally used as an intermediate.

A light emission device utilizing the iridium complex produced by the producing method of the present invention can be used in a product requiring an energy saving or a high luminance. Application examples include a display apparatus, an illumination apparatus, a light source for a printer, and a backlight for a liquid crystal display apparatus. These apparatuses are equipped with a unit for supplying the organic EL device with an electrical signal. The display apparatus can be realized as a flat panel display capable of achieving an energy saving, high visibility and light weight. As a light source for a printer, a laser light source unit widely used in laser beam printers may be replaced by the light emission device of the present invention. In this case, independently addressable devices are arranged in an array to provide a photosensitive drum with desired exposure, thereby forming images. The device of the present invention enables the volume of the apparatus to be significantly reduced. With the illuminating apparatus and the backlight, the present invention is expected to provide an energy saving effect.

In the application to a display, a drive system utilizing a TFT drive circuit of an active matrix system is conceivable.

In the following, an exemplary embodiment in which an active matrix substrate is used in the device of the present invention will be described with reference to FIGS. 4 to 6.

Figure 4:
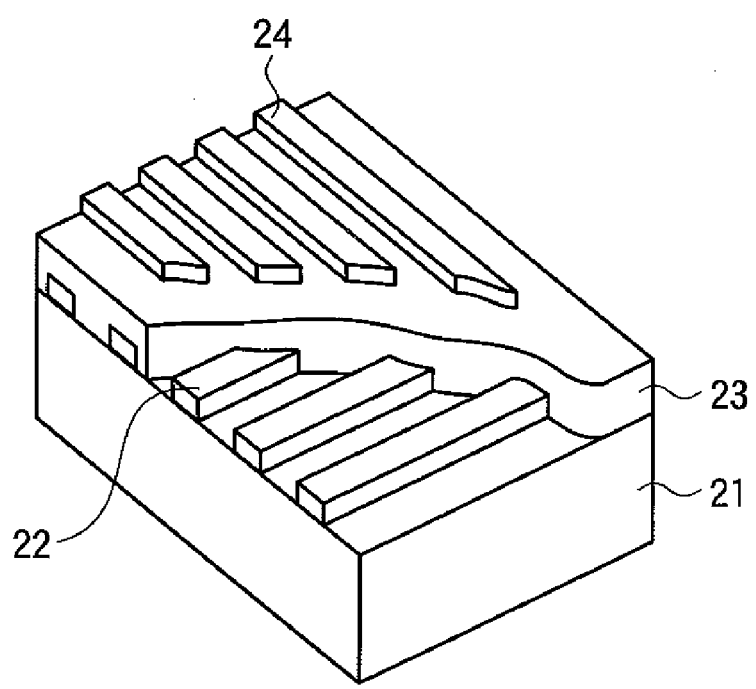
FIG. 4 is a schematic view of a passive type of organic EL device.
Figure 5:
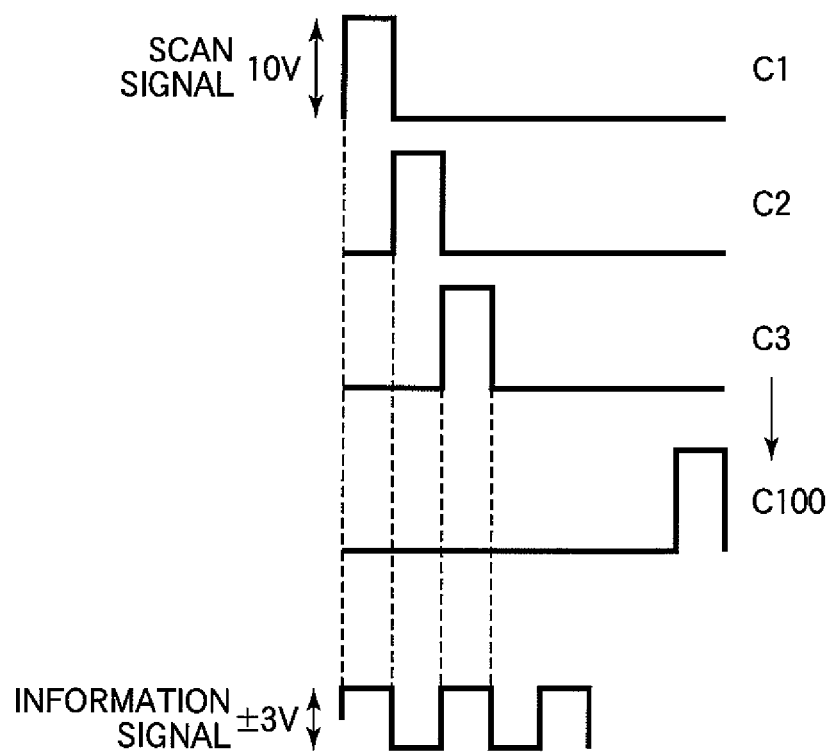
FIG. 5 is a view illustrating a pixel circuit of a panel.

FIG. 4 schematically illustrates an example of a passive type of EL device. In FIG. 4, 21 denotes a glass substrate; 22, An ITO electrode; 23, an organic compound layer; and 24, a cathode. The panel is equipped with a scan signal driver, an information signal driver and a current supply source, which are connected respectively to gate selecting lines, information signal lines and current supply lines. A pixel circuit illustrated in FIG. 5 is placed at the intersection point between the gate selecting line and the information signal line. The scan signal driver selects the gate selecting lines G1, G2, G3, ... , Gn in succession, and in synchronization therewith, image signals are applied from the information signal driver.

Next, the operation of the pixel circuit will be described. In the pixel circuit, when a selection signal is applied to the gate selecting line, a TFT 1 is turned on to supply Cadd with an image signal, thereby determining a gate potential of TFT 2. The EL device is supplied with a current from the current supply line according to the gate potential of TFT 2. The gate potential of TFT 2 is maintained at the potential of Cadd until the TFT 1 is selected in a next scan, so that the current continues to flow in the EL device until the next scan. Thus, the light emission can be maintained constantly during a one frame period.

Figure 6:
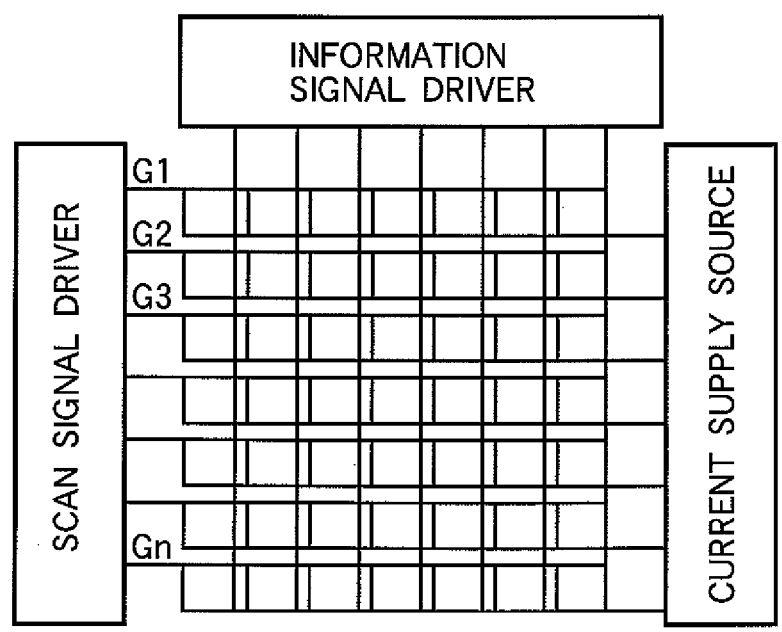
FIG. 6 is a schematic view illustrating an example of a TFT substrate to be employed in the present invention.

FIG. 6 is a schematic view illustrating an example of a TFT substrate employed in the present invention. A p-Si layer is formed on a glass substrate, and necessary impurities are doped respectively in channel, drain and source areas. A gate electrode is formed thereon with intervention of a gate insulation film, and a drain electrode and a source electrode are so formed as to be connected to the drain area and the source area. Then, an insulation layer and an ITO electrode as a pixel electrode are superimposed thereon, and the ITO and the drain electrode are connected through a contact hole.

In the present invention, a switching element is not particularly limited, and a single crystal silicon substrate, an MIM device or an a-Si device may be easily adopted.

An organic EL display panel can be obtained by superimposing, on the ITO electrode, a multi-layered or single-layered organic EL layer/cathode layer in succession. The display panel utilizing the iridium complex of the present invention can constantly display images having satisfactory image quality over a long period of time.

Specific structures of the iridium complex used in the present invention will be shown below, where a portion bonded to Ir is represented by a bond illustrated by the following general formula (A):

(A)

A1 to A25 illustrate examples of the 4-membered ring ligand skeleton possessed by the raw material compound for the iridium complex. B1 to B76 illustrate examples of the light emitting ligand of the iridium complex.

C1 to C77 illustrate examples of the iridium complex having the ligands of from A1 to A25 and of from B1 to B76. D1 to D97 illustrate examples of the iridium complex for use in a light emission device, that can be synthesized through the intermediate of from A1 to A25 and by combining B1 to B76 and C1 to C77.

Due to such combinations, iridium complexes having 4-membered ring structures can be synthesized, and using the iridium complexes as raw materials, iridium complexes can be synthesized.

However, the following only shows typical examples, and the present invention is by no means limited thereto.

A1

-continued
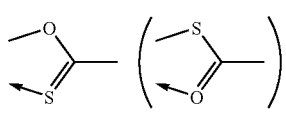
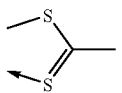
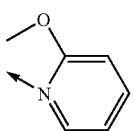
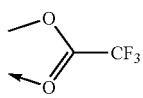
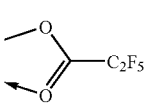
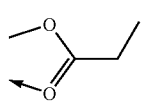
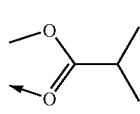
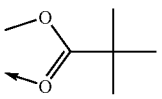
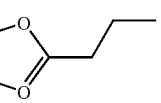
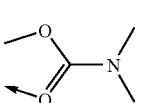
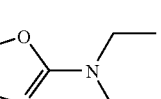
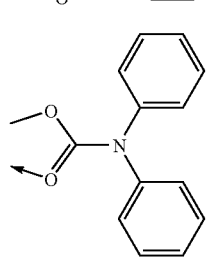
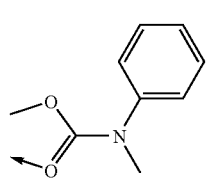
-continued
A2
A3
A4
A5
A6
A7
A8
A9
A10
A11
A12
A13
A14
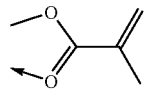
A15
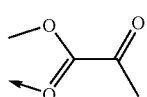
A16
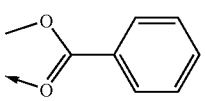
A17
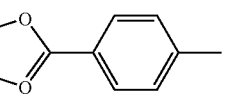
A18
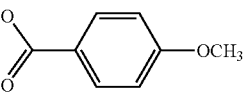
A19
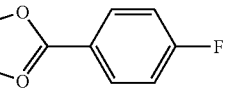
A20
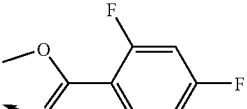
A21
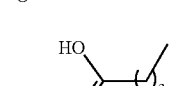
A22
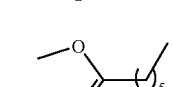
A23
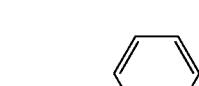
A24
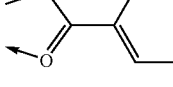
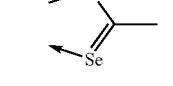
A25
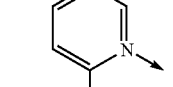
B1

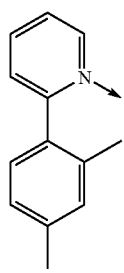 B2
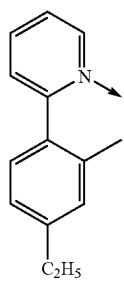 B3
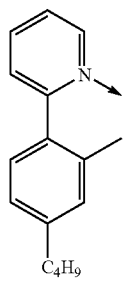 B4
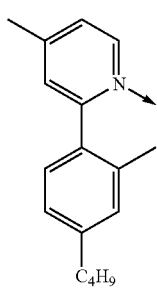 B5
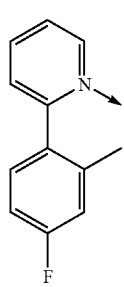 B6
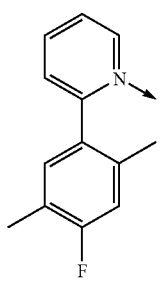 B7
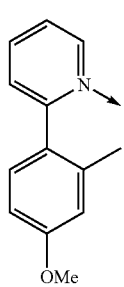 B8
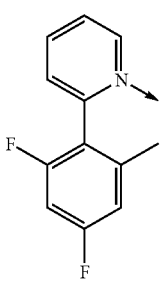 B9
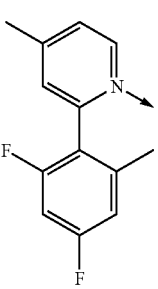 B10
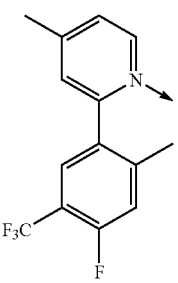 B11

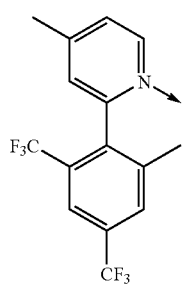 B12
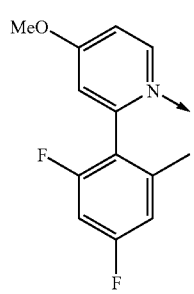 B13
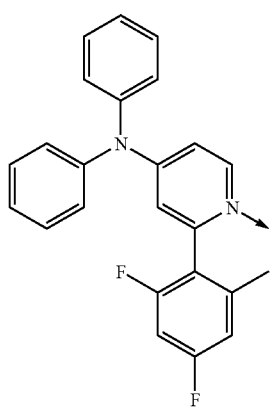 B14
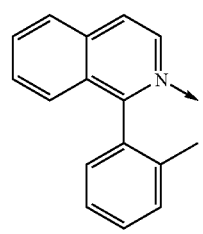 B15
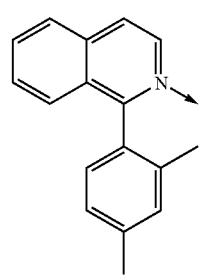 B16
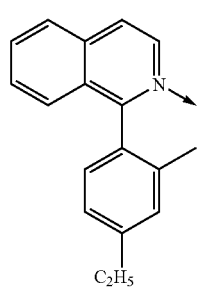 B17
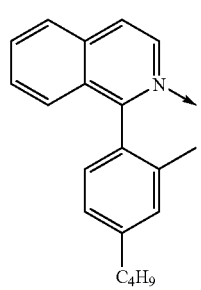 B18
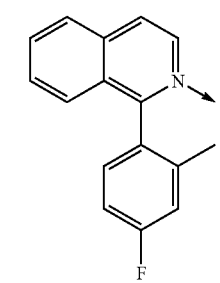 B19
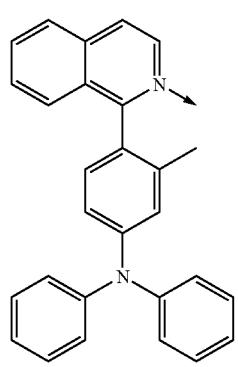 B20
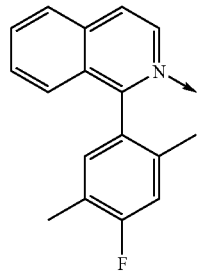 B21

| | |
|---|---|
| 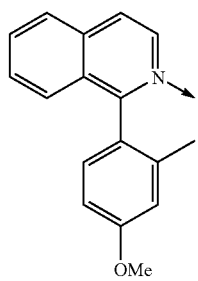 B22 | 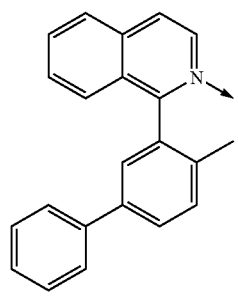 B27 |
| 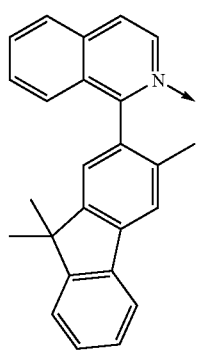 B23 | 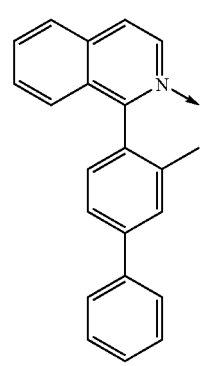 B28 |
| 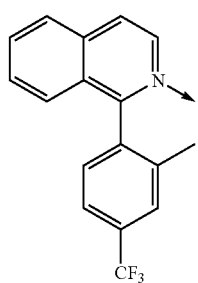 B24 | 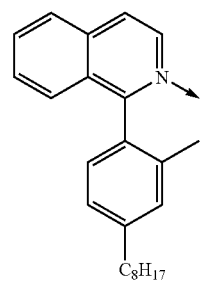 B29 |
| 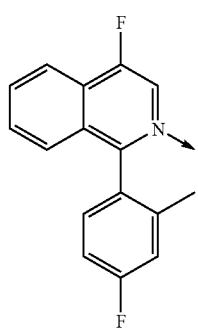 B25 | 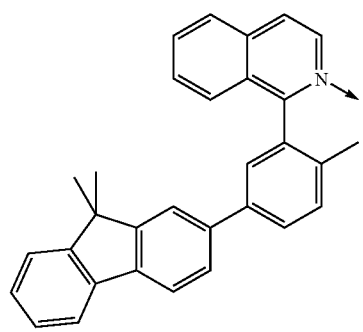 B30 |
| 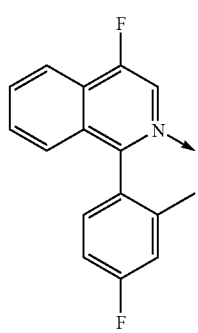 B26 | 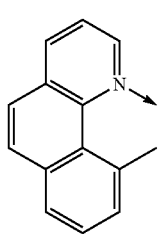 B31 |

-continued
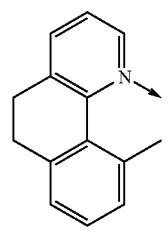
B32
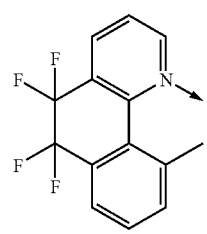
B33
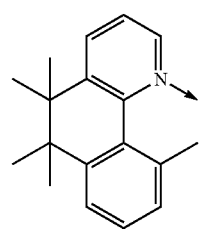
B34
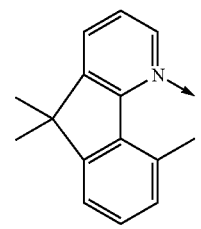
B35
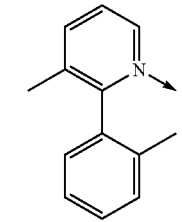
B36
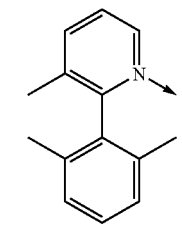
B37
-continued
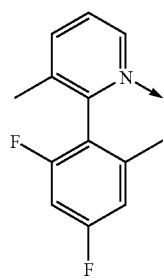
B38
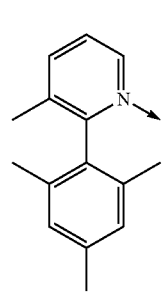
B39
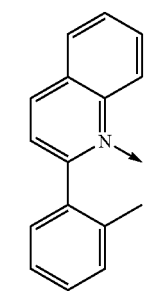
B40
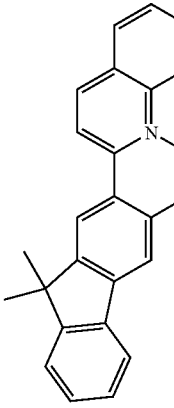
B41
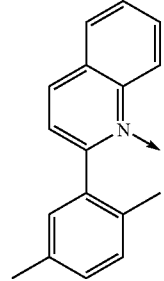
B42

B43 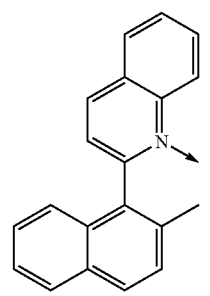
B44 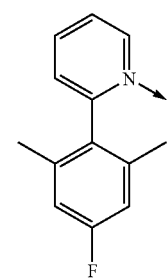
B45 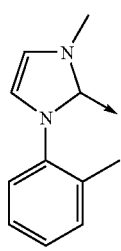
B46 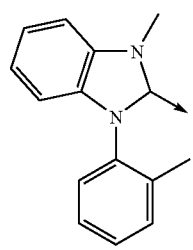
B47 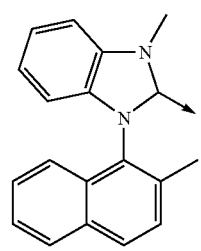
B48 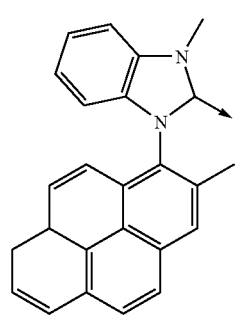
B49 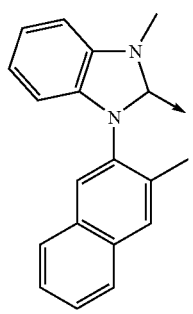
B50 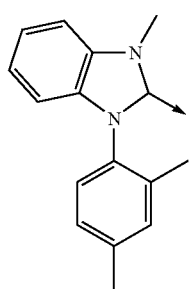
B51 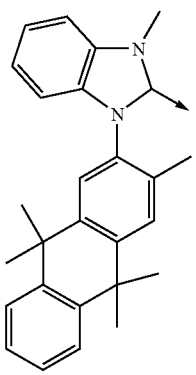
B52 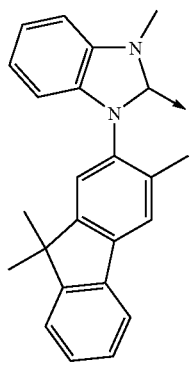
B53 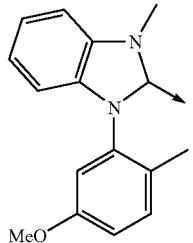

-continued
B54
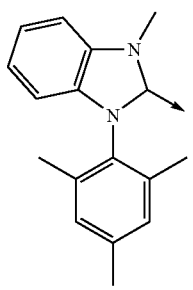
B55
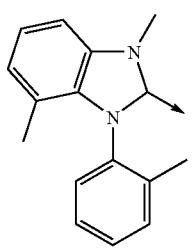
B56
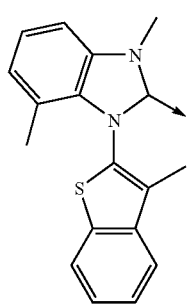
B57
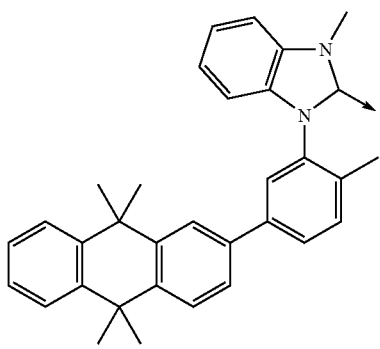
B58
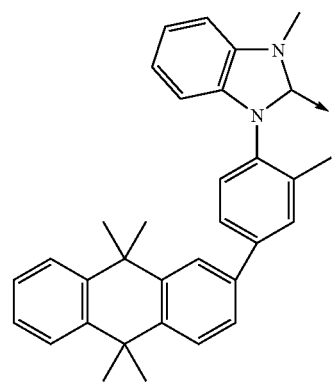
-continued
B59
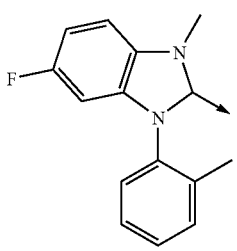
B60
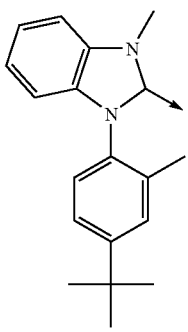
B61
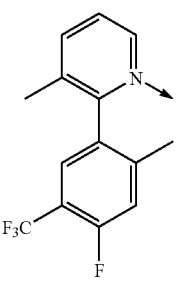
B62
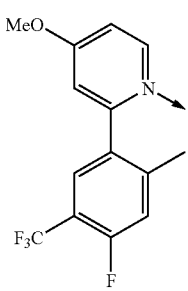
B63
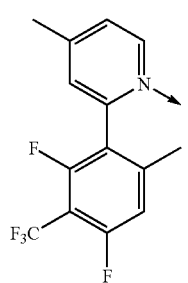

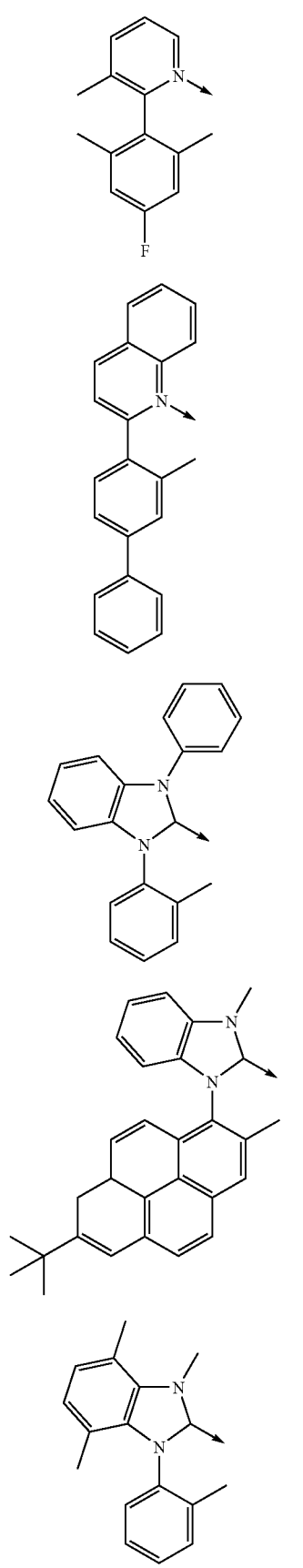
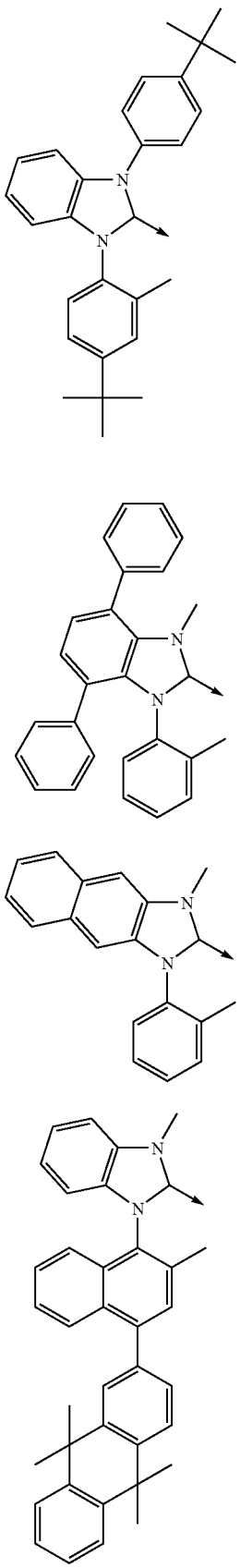

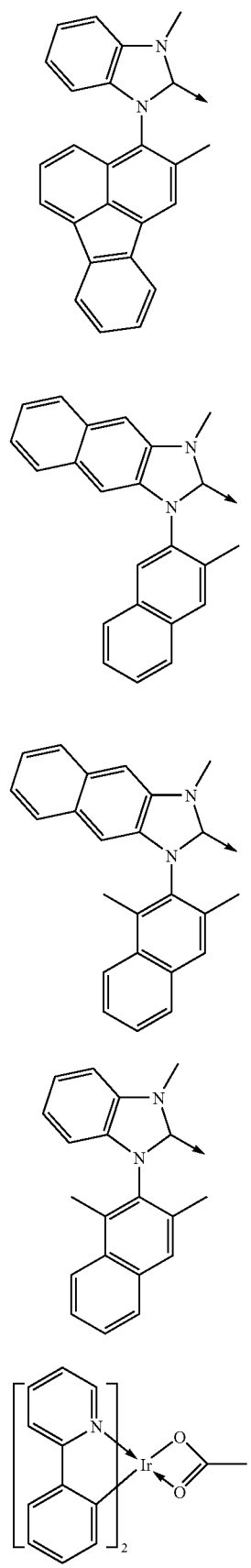
B73
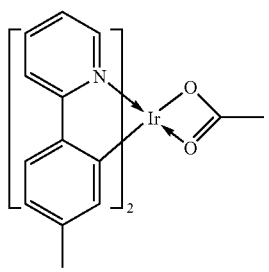
B74
C3
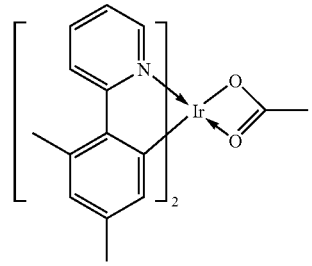
C4
B75
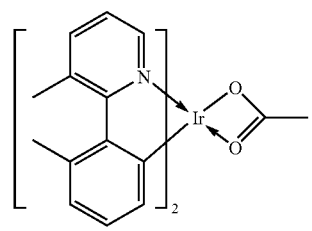
C5
B76
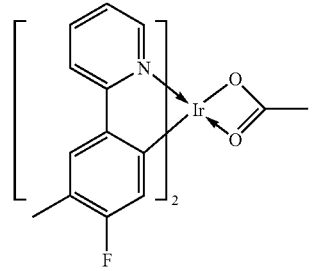
C1
C6
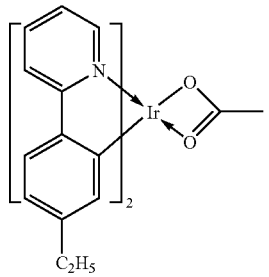
C7
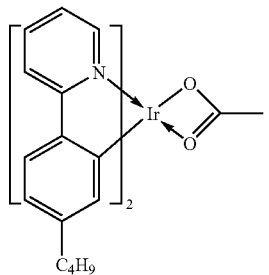

-continued
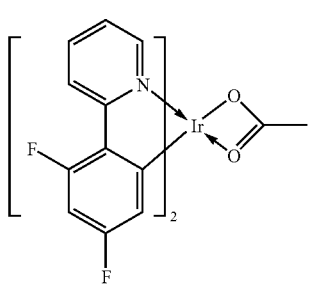 C8
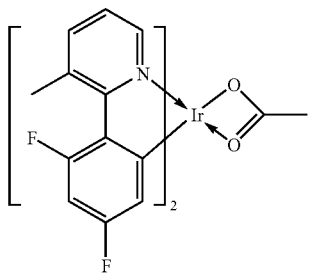 C9
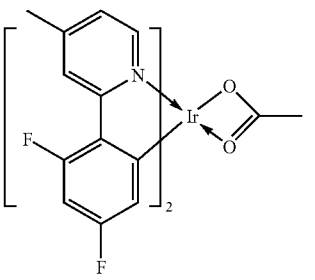 C10
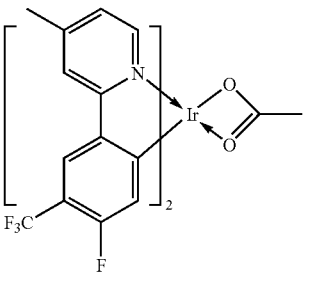 C11
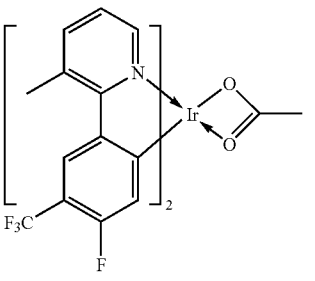 C12
-continued
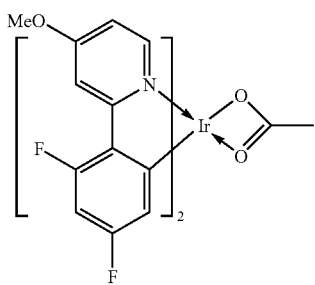 C13
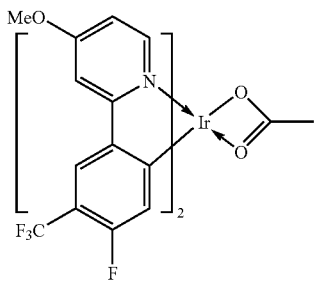 C14
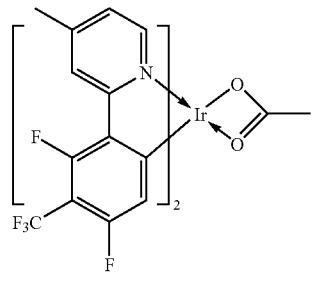 C15
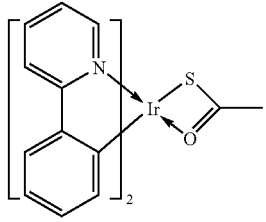 C16
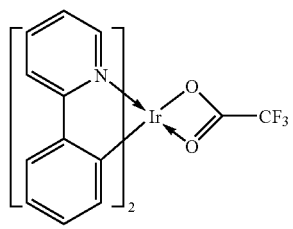 C17
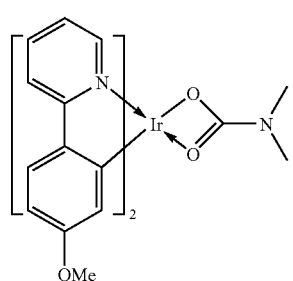 C18

-continued
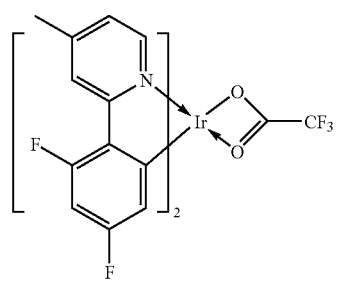
C19
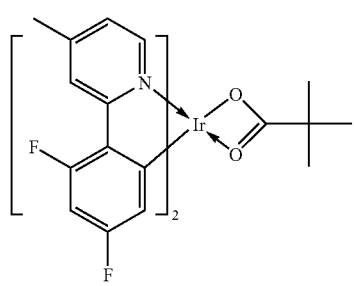
C20
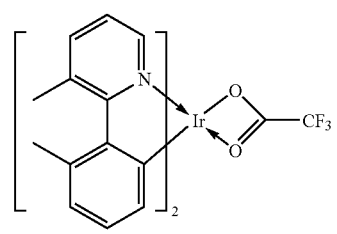
C21
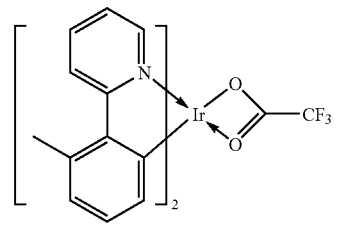
C22
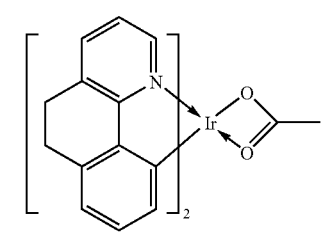
C23
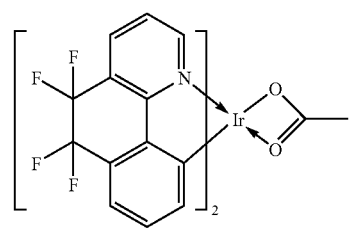
C24
-continued
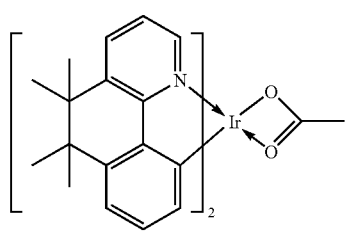
C25
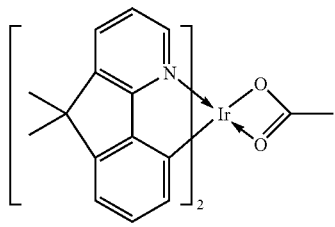
C26
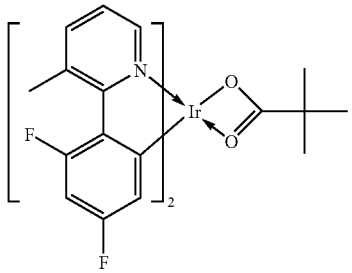
C27
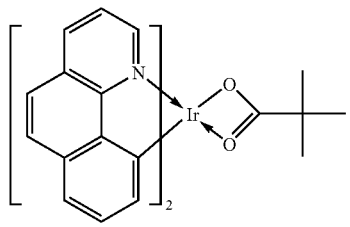
C28
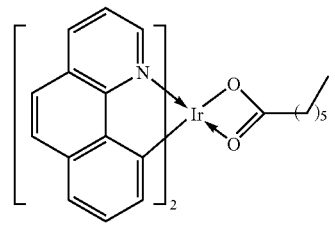
C29
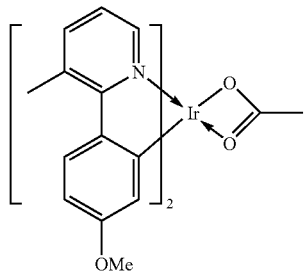
C30

C31 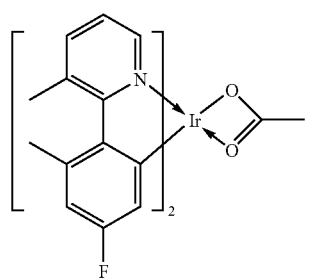
C32 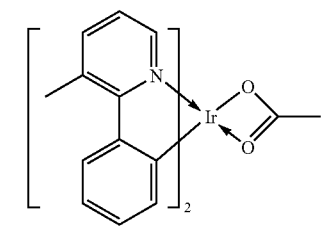
C33 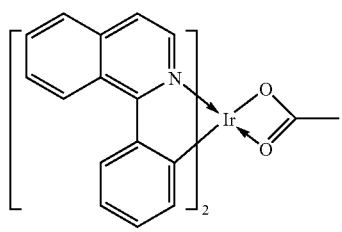
C34 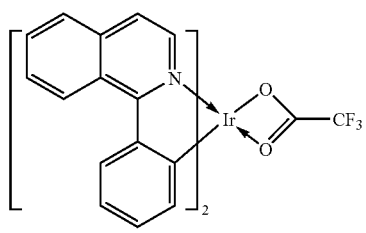
C35 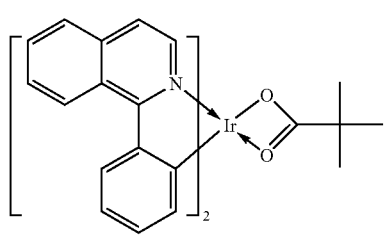
C36 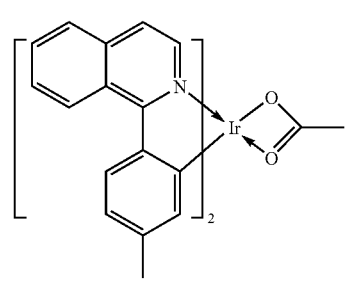
C37 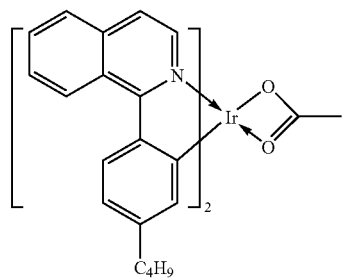
C38 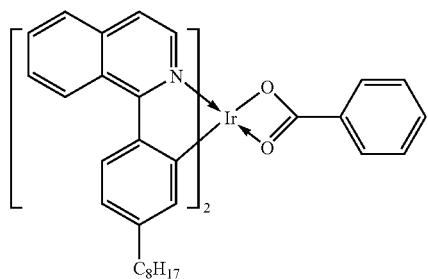
C39 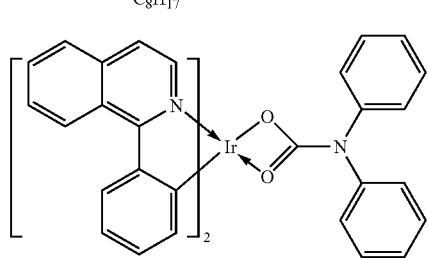
C40 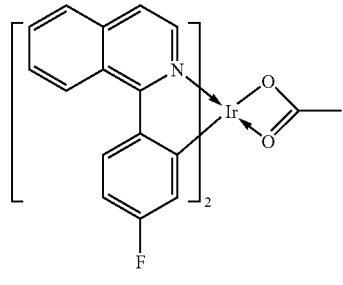
C41 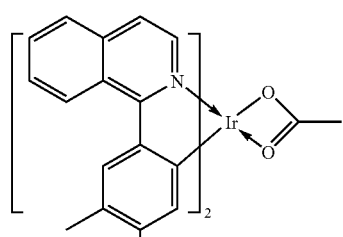
C42 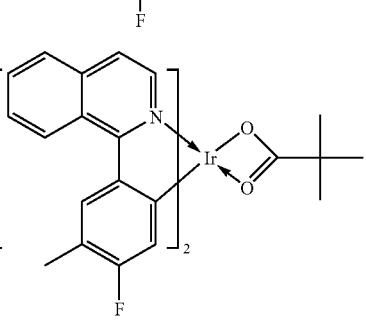

-continued
C43
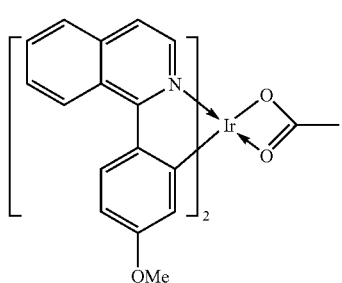
C44
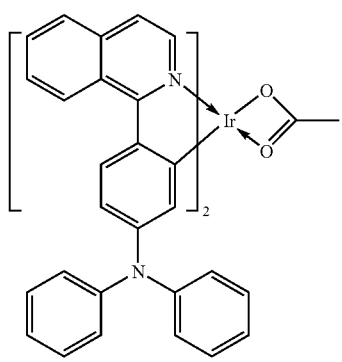
C45
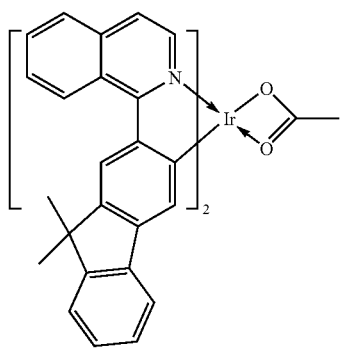
C46
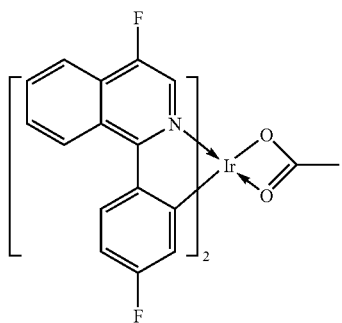
C47
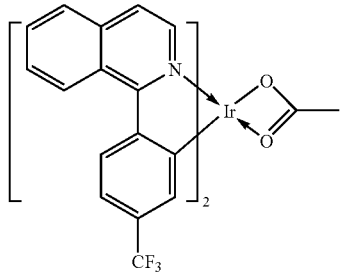
-continued
C48
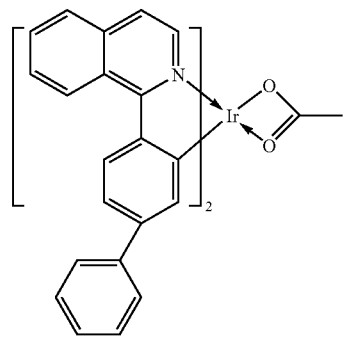
C49
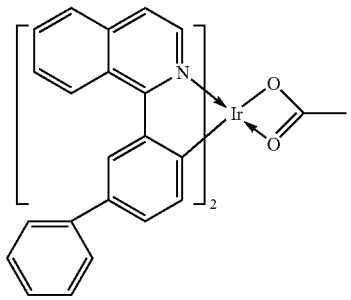
C50
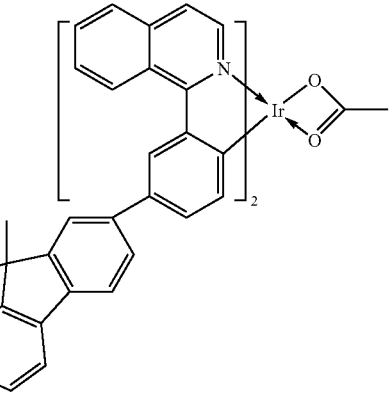
C51
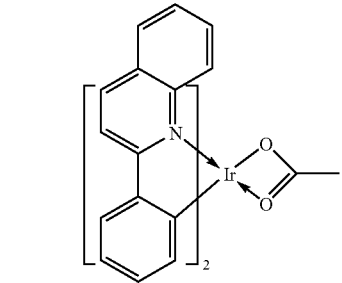

C52
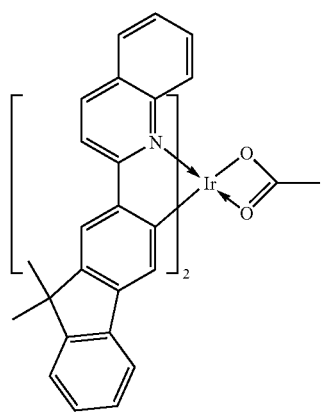
C53
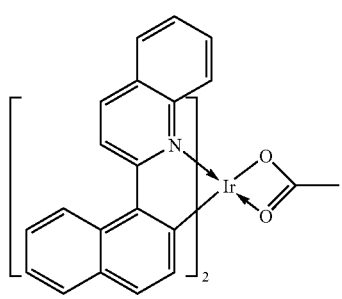
C54
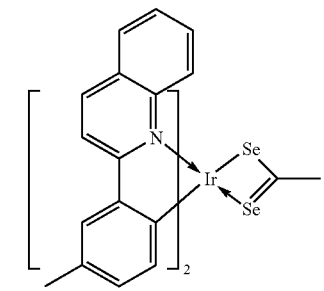
C55
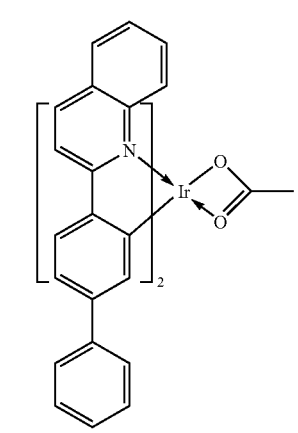
C56
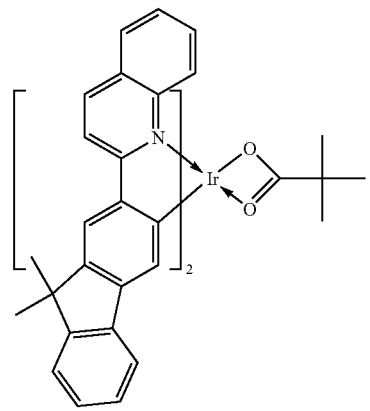
C57
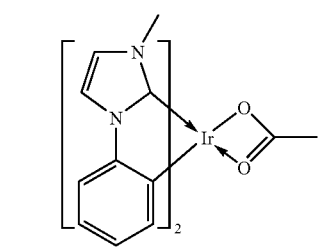
C58
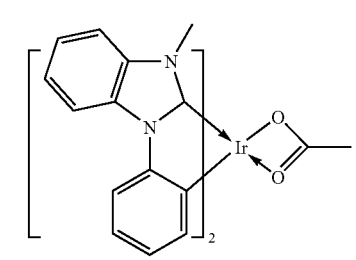
C59
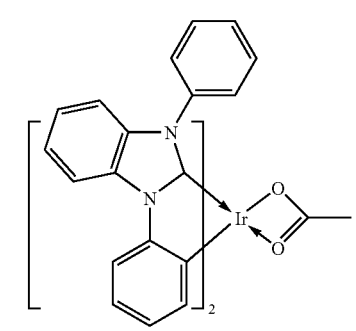
C60
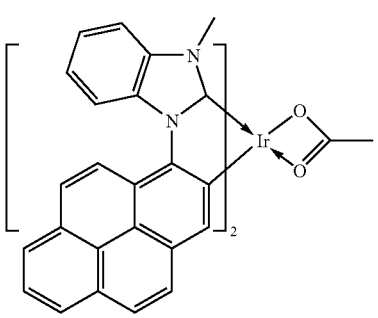

C61 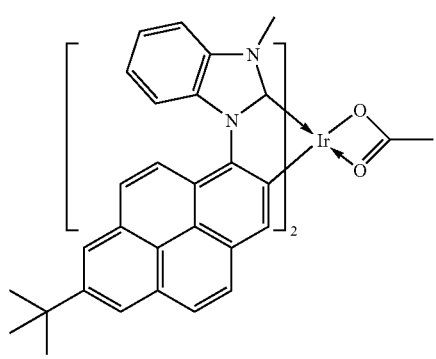
C62 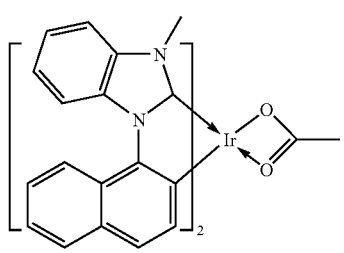
C63 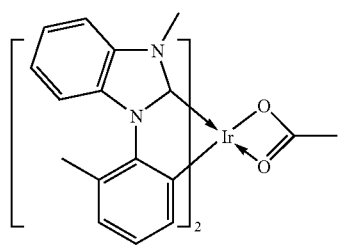
C64 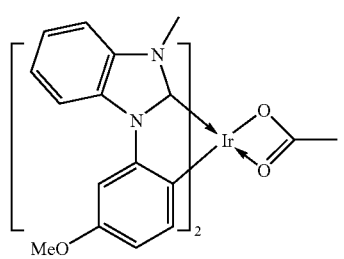
C65 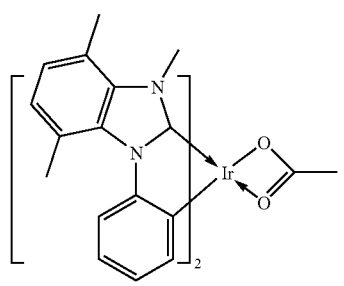
C66 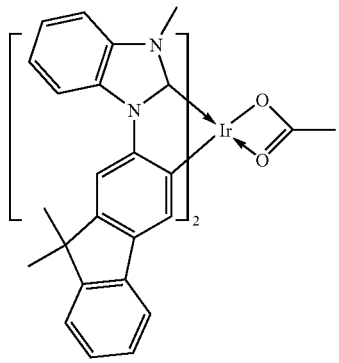
C67 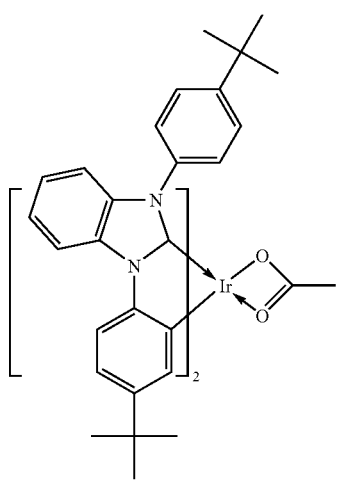
C68 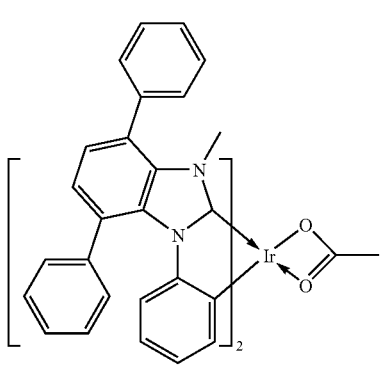
C69 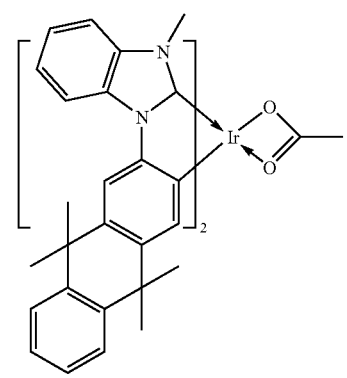

C70
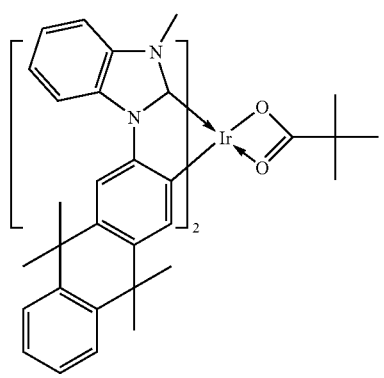
C71
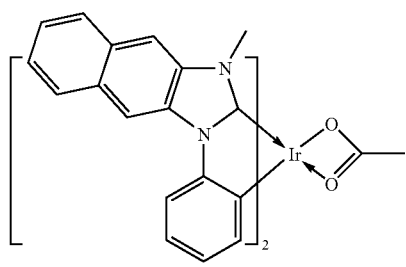
C72
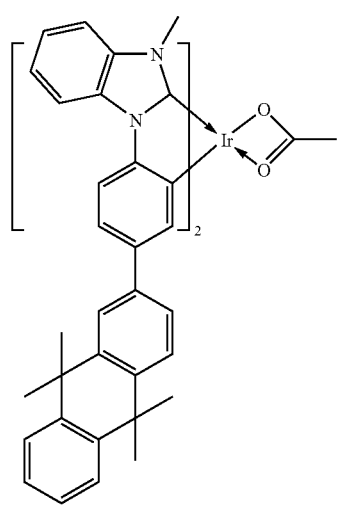
C73
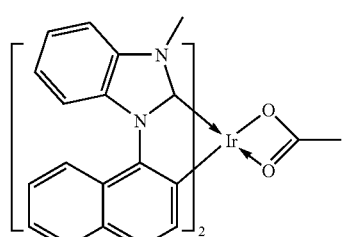
C74
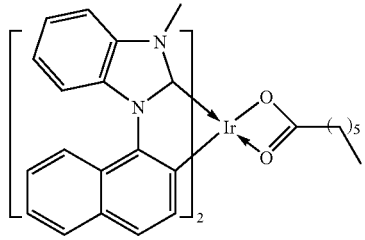
C75
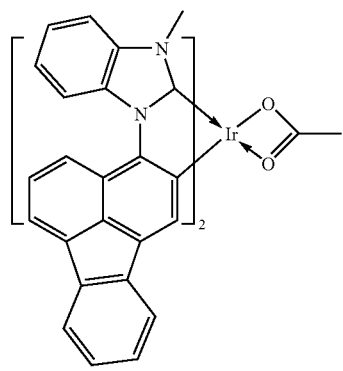
C76
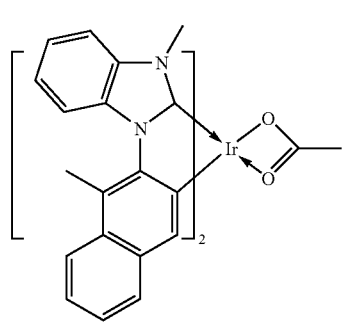
C77
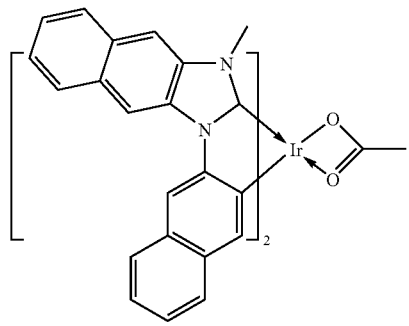
D1
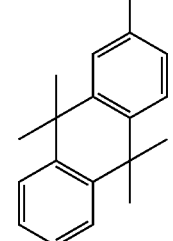

-continued
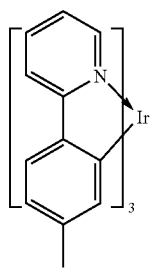 D2
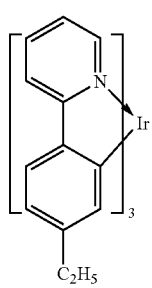 D3
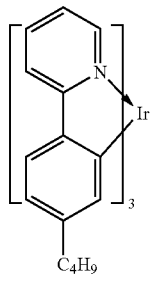 D4
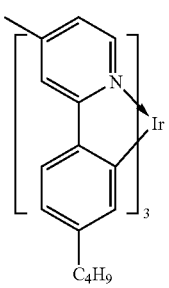 D5
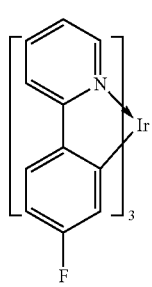 D6
-continued
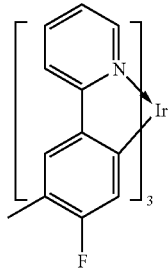 D7
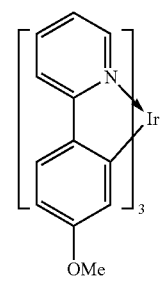 D8
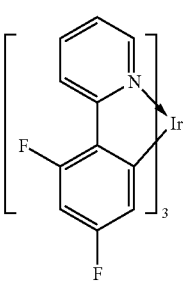 D9
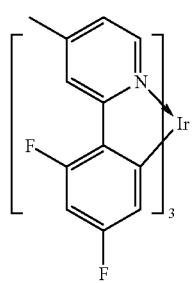 D10
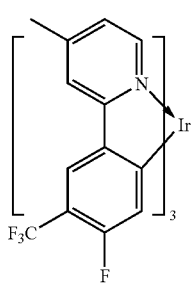 D11

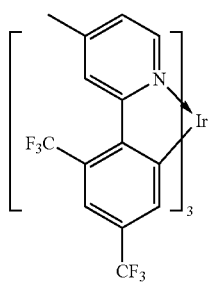 D12
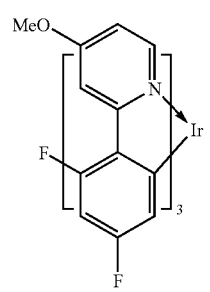 D13
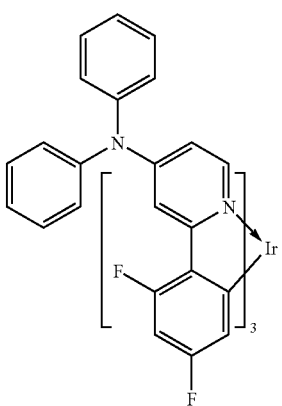 D14
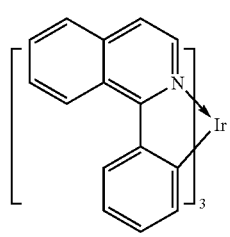 D15
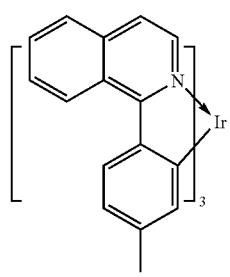 D16
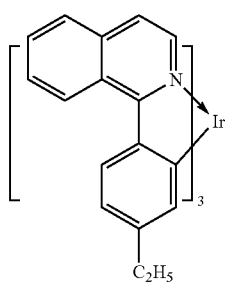 D17
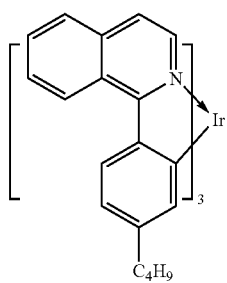 D18
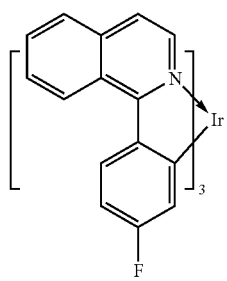 D19
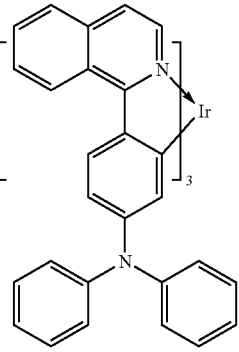 D20
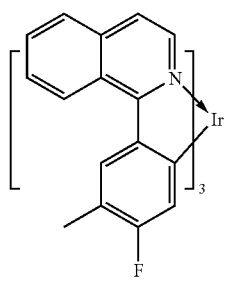 D21

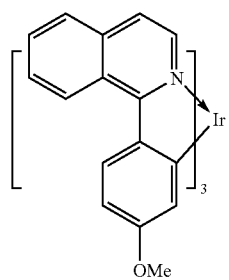 D22
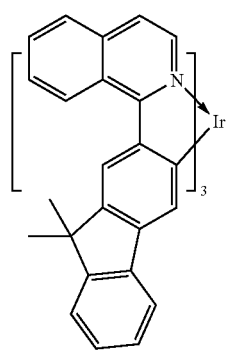 D23
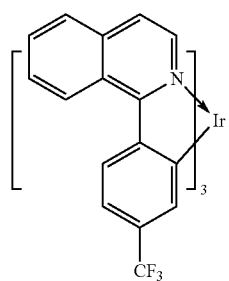 D24
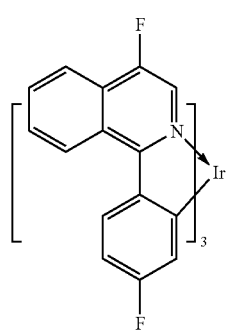 D25
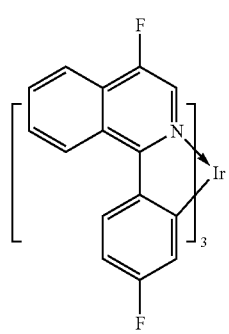 D26
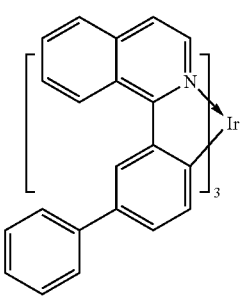 D27
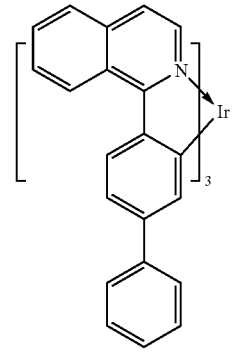 D28
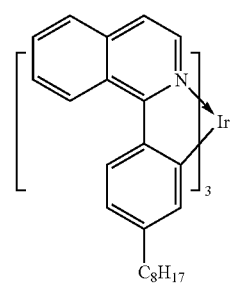 D29
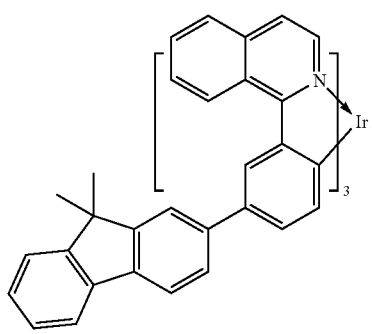 D30
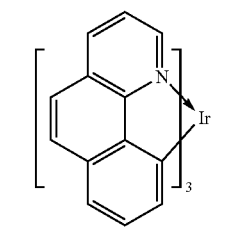 D31

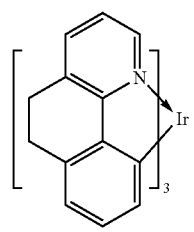 D32
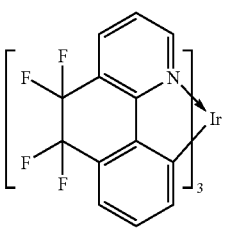 D33
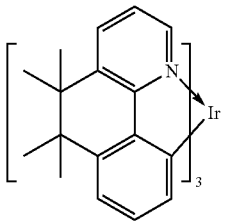 D34
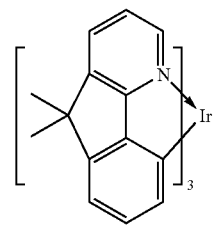 D35
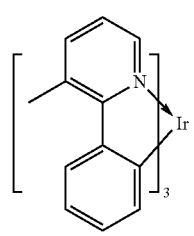 D36
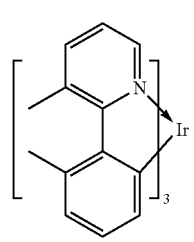 D37
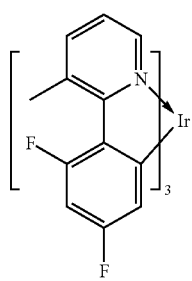 D38
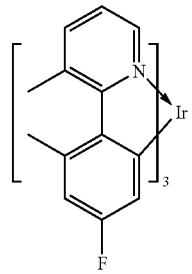 D39
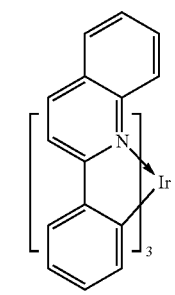 D40
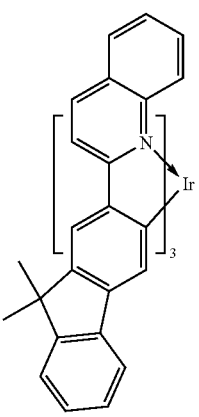 D41
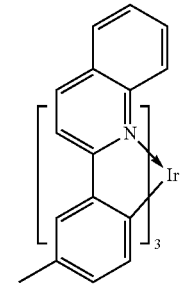 D42

D43
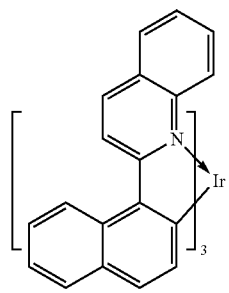
D44
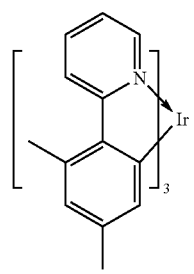
D45
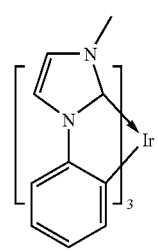
D46
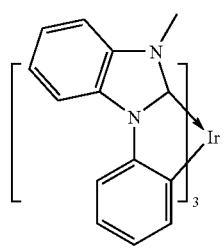
D47
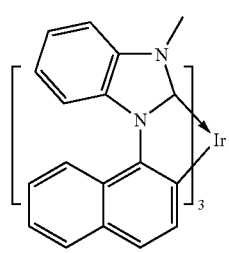
D48
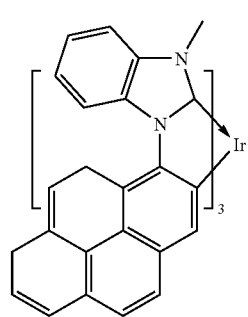
D49
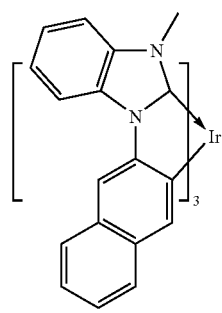
D50
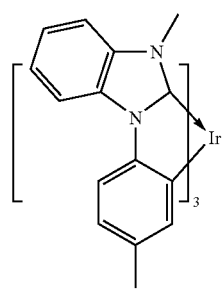
D51
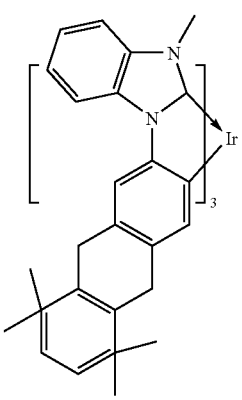
D52
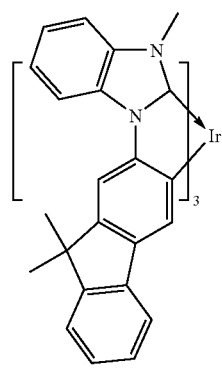
D53
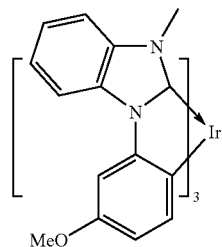

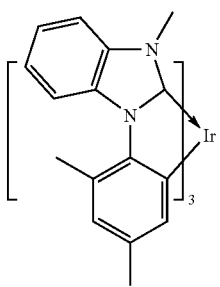
D54
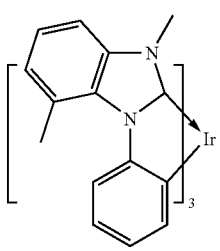
D55
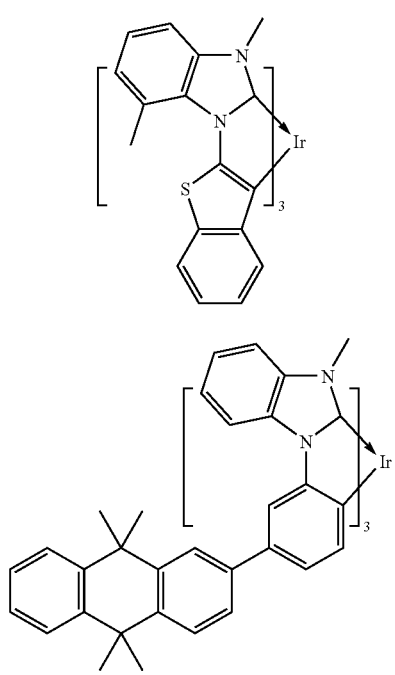
D56
D57
D58
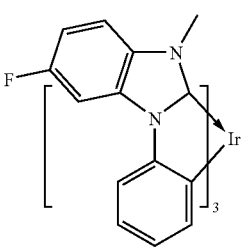
D59
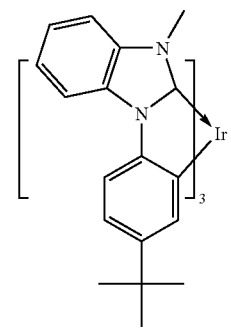
D60
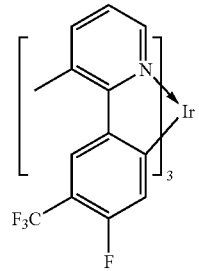
D61
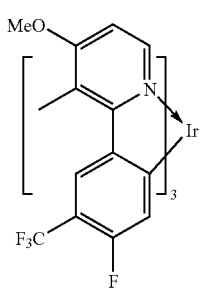
D62
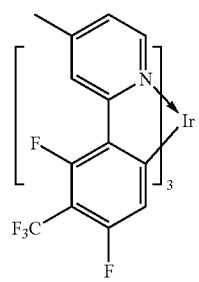
D63

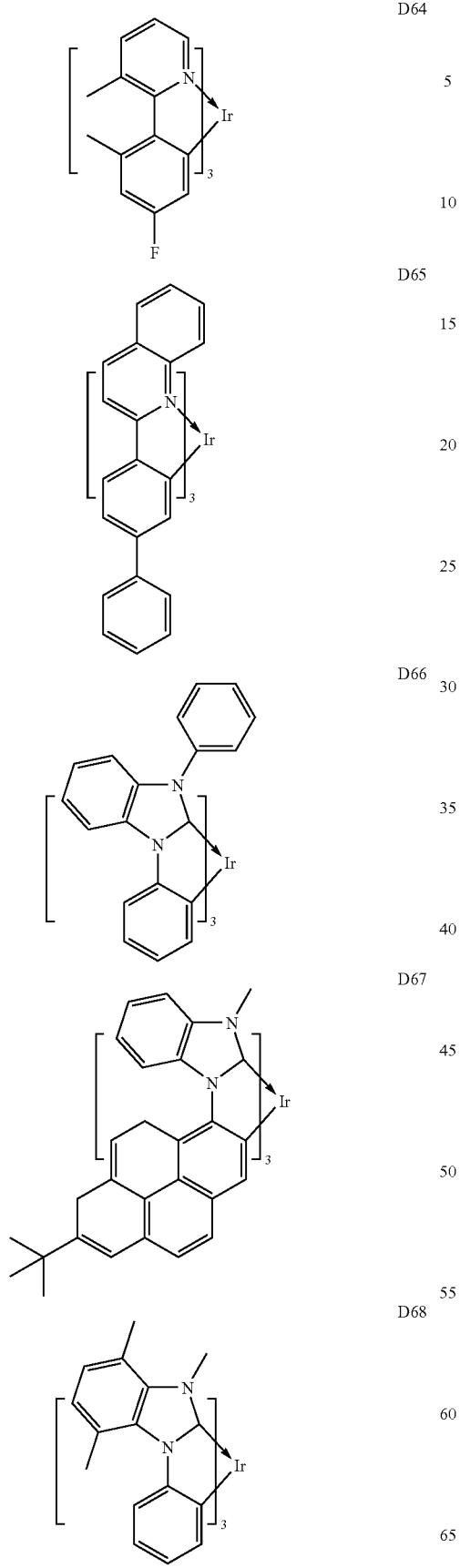

D73
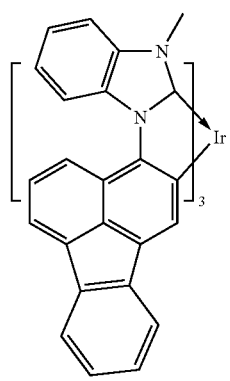
D74
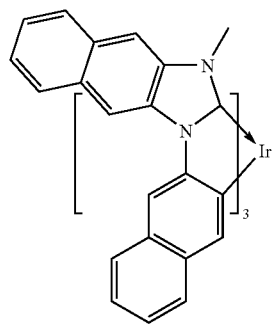
D75
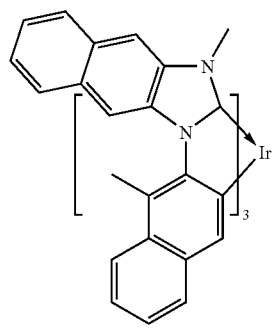
D76
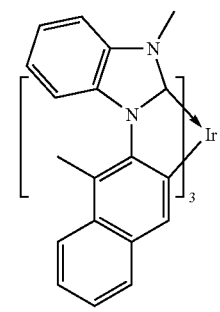
D77
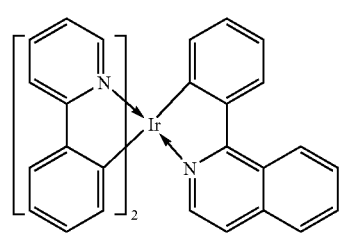
D78
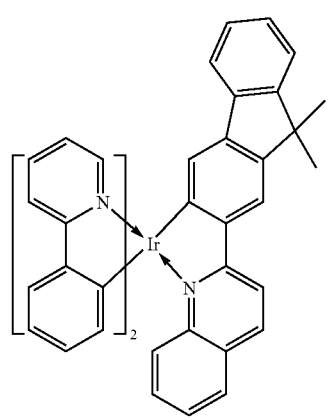
D79
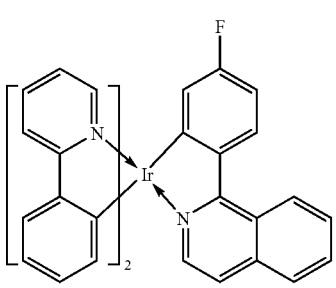
D80
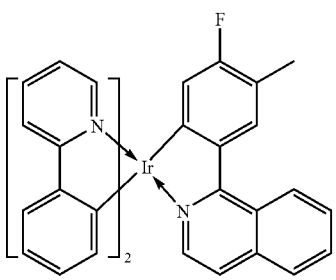
D81
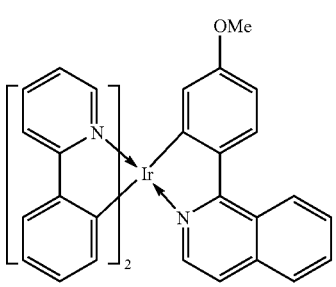
D82
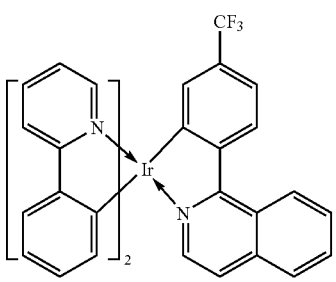

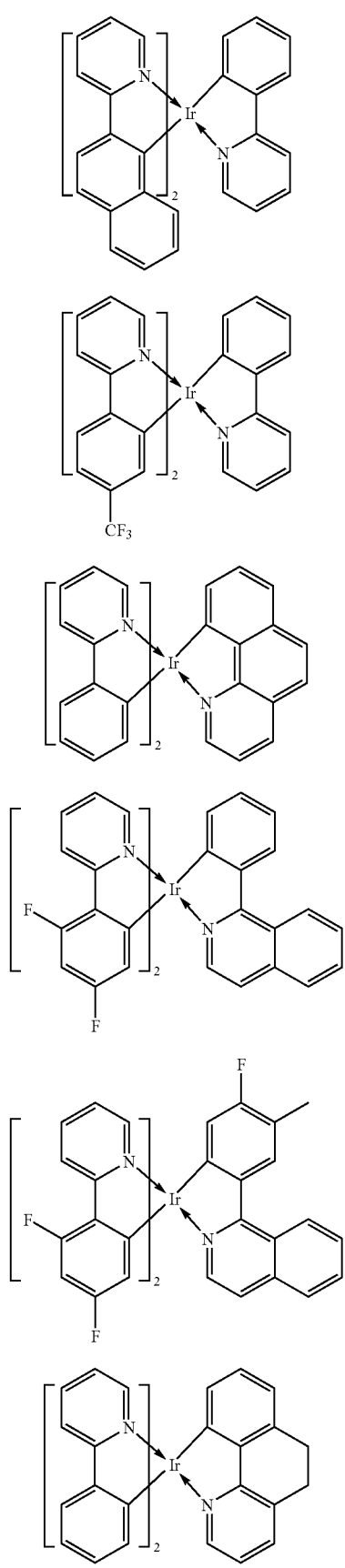
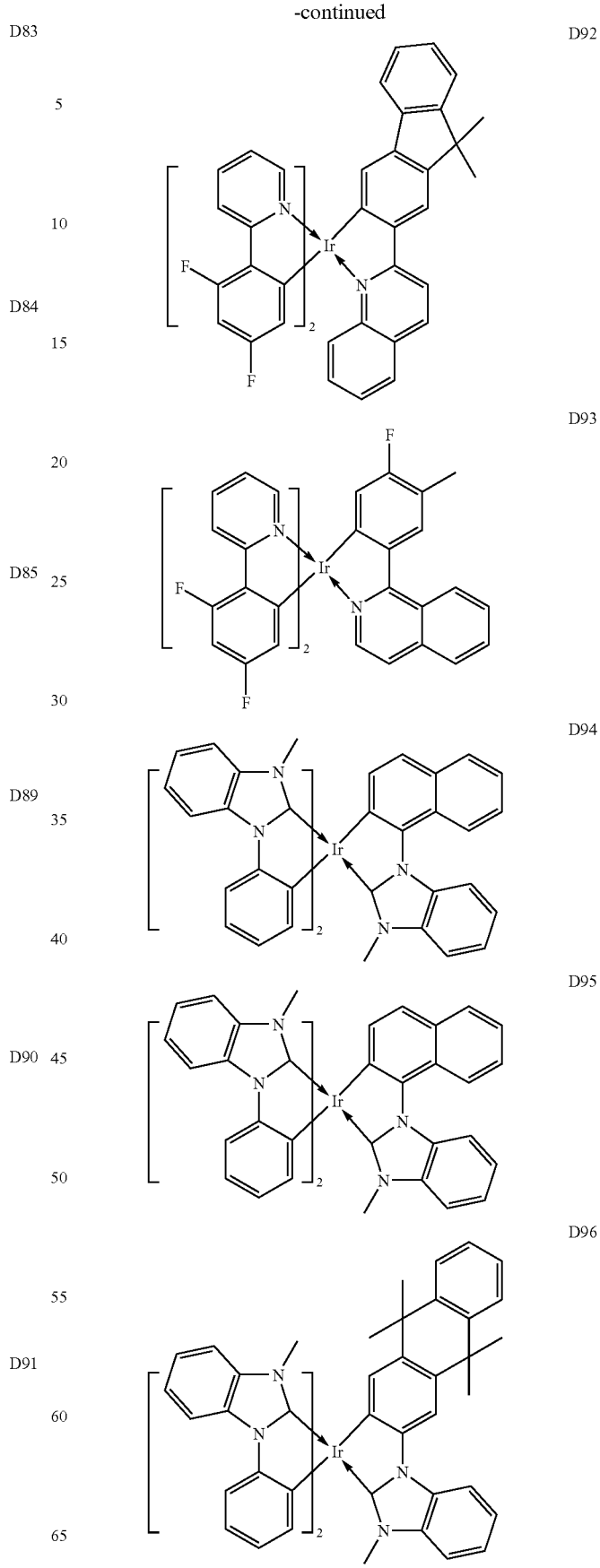

-continued

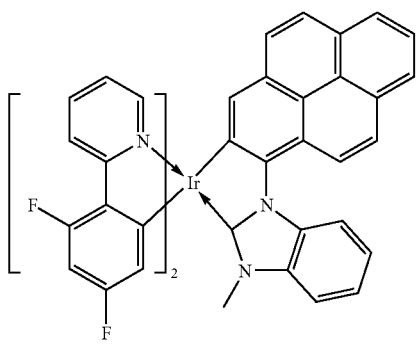

D97

EMBODIMENTS

In the following, the present invention will be clarified in detail by exemplary embodiments, but the present invention is not limited to such exemplary embodiments.

As to the synthesizing process required for synthesizing the exemplary compounds, typical synthesis embodiments will be described below.

Exemplary Synthesis 1

Method of Producing Compound No. D21 by Using an Exemplary Compound No. C41 as Intermiate

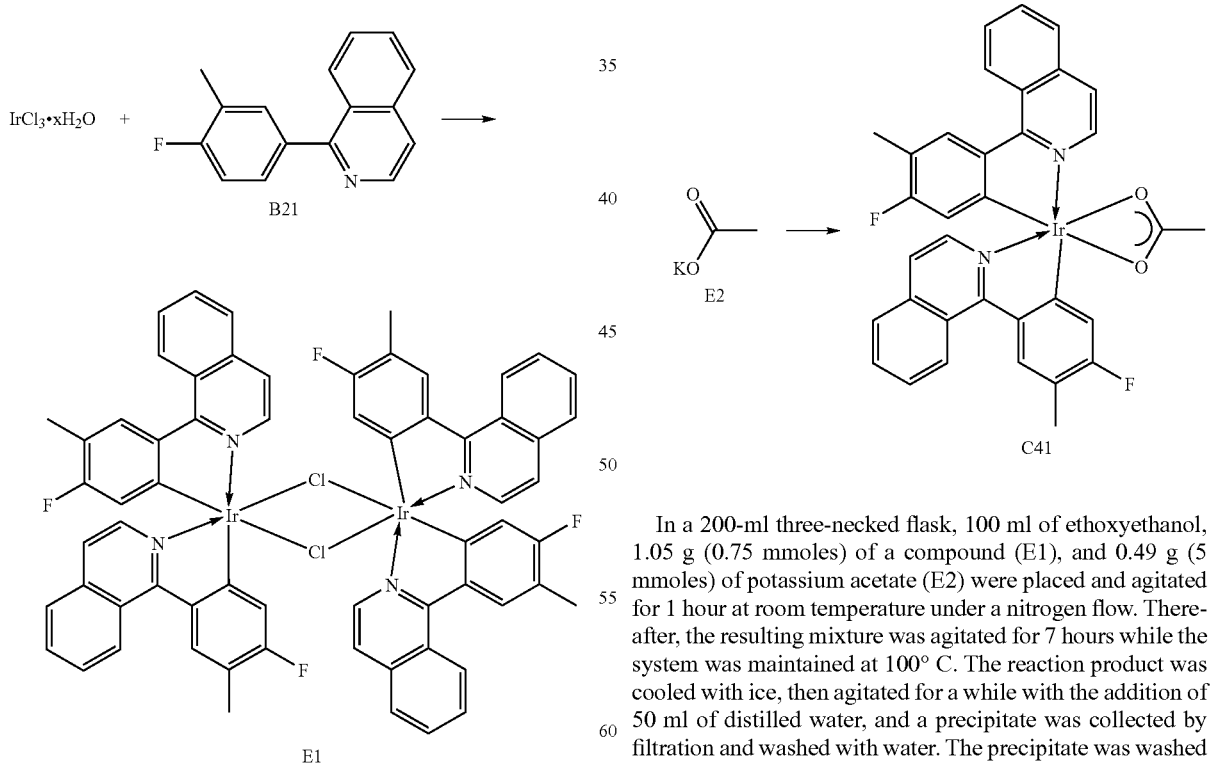

In a 200-ml three-necked flask, 0.71 g (2 mmoles) of iridium (III) trihydrate, 1.90 g (8 moles) of a compound (B21), 90 ml of ethoxyethanol and 30 ml of water were placed, and agitated for 30 minutes at room temperature under a nitrogen flow. Then, the resulting mixture was agitated under reflux for 10 hours. The reaction product was cooled to room temperature, and a precipitate was collected by filtration, washed with water, and then washed with ethanol. The precipitate was dried under a reduced pressure at room temperature to produce 1.20 g (yield 86%) of a compund (E1) as a red-colored powder.

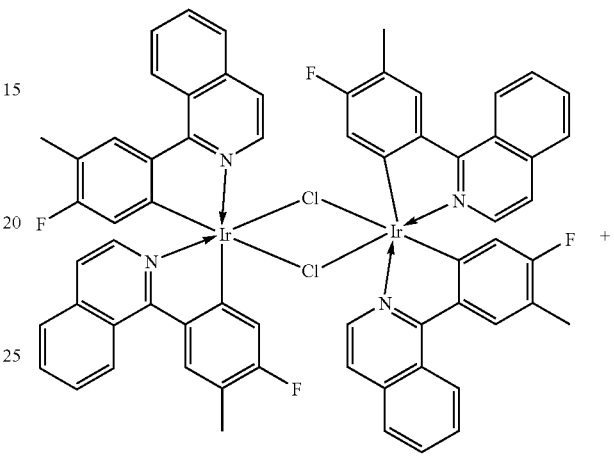

In a 200-ml three-necked flask, 100 ml of ethoxyethanol, 1.05 g (0.75 mmoles) of a compound (E1), and 0.49 g (5 mmoles) of potassium acetate (E2) were placed and agitated for 1 hour at room temperature under a nitrogen flow. Thereafter, the resulting mixture was agitated for 7 hours while the system was maintained at 100° C. The reaction product was cooled with ice, then agitated for a while with the addition of 50 ml of distilled water, and a precipitate was collected by filtration and washed with water. The precipitate was washed with ethanol and dissolved in chloroform, and an undissolved substance was filtered off. The filtrate was concentrated and recrystallized from chloroform-methanol to produce 9.24 g (yield 85%) of an exemplary compound No. C41 as a red-colored powder. MALDI-TOF MS confirmed M+ of this compound as 724.15.

Exemplary Synthesis 2

Method of Producing Exemplary Compound No. C41 as Intermediate

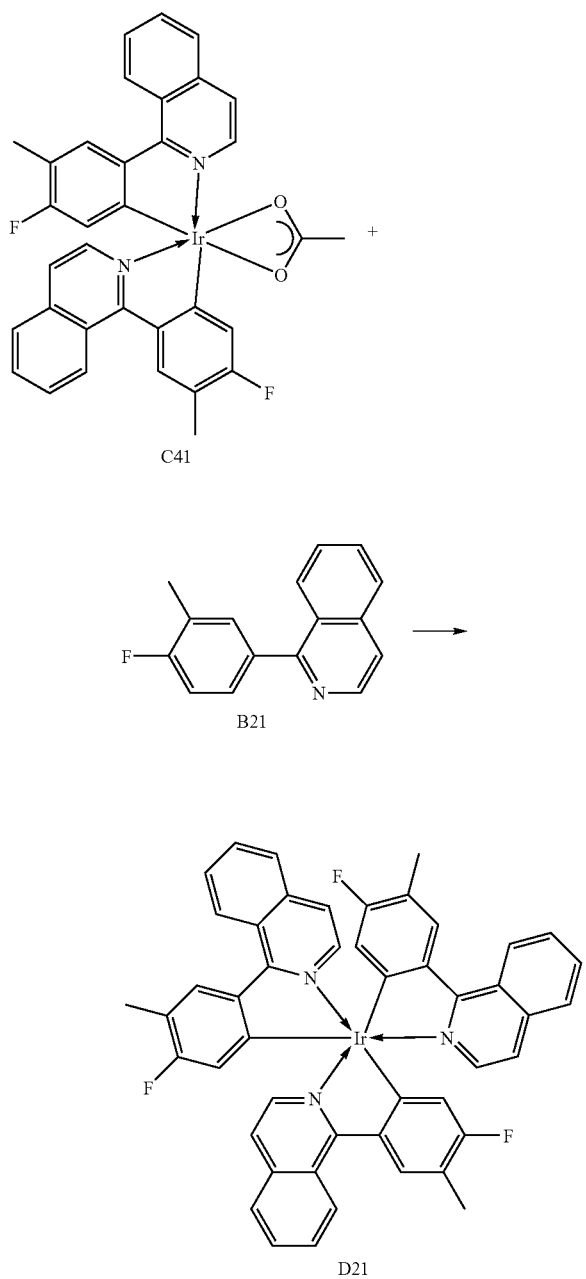

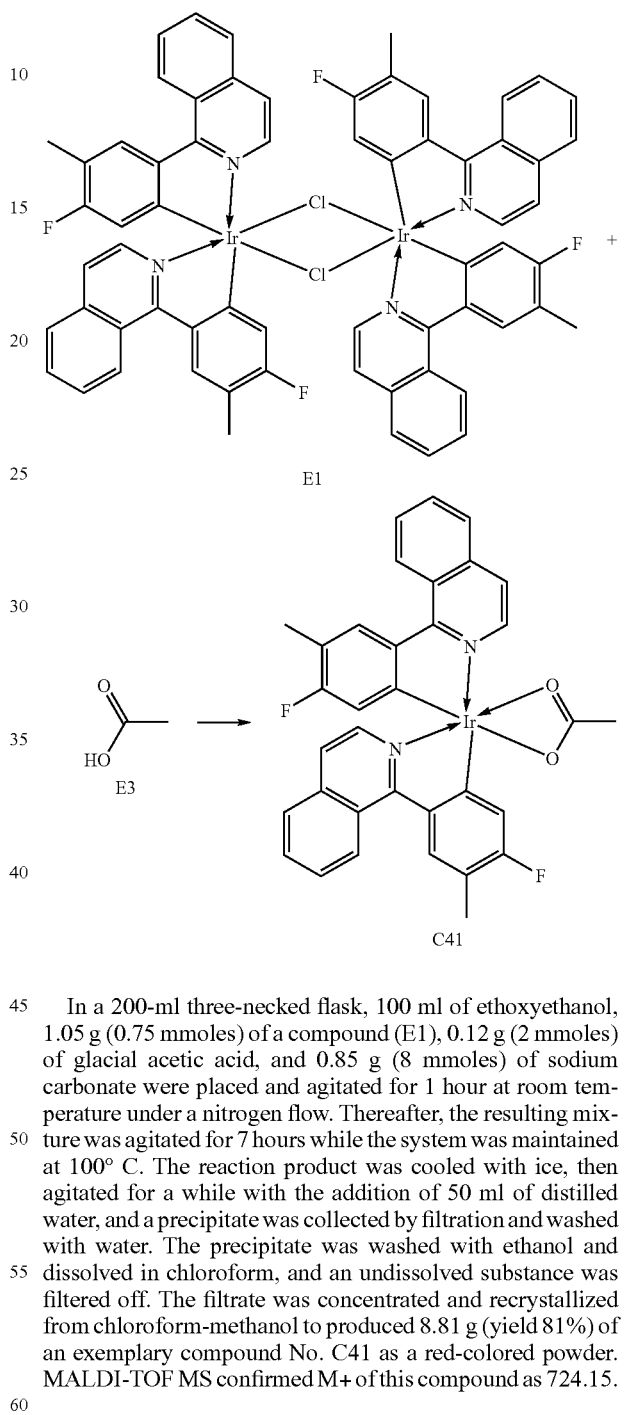

In a 200-ml three-necked flask, 100 ml of ethoxyethanol, 1.05 g (0.75 mmoles) of a compound (E1), 0.12 g (2 mmoles) of glacial acetic acid, and 0.85 g (8 mmoles) of sodium carbonate were placed and agitated for 1 hour at room temperature under a nitrogen flow. Thereafter, the resulting mixture was agitated for 7 hours while the system was maintained at 100° C. The reaction product was cooled with ice, then agitated for a while with the addition of 50 ml of distilled water, and a precipitate was collected by filtration and washed with water. The precipitate was washed with ethanol and dissolved in chloroform, and an undissolved substance was filtered off. The filtrate was concentrated and recrystallized from chloroform-methanol to produced 8.81 g (yield 81%) of an exemplary compound No. C41 as a red-colored powder. MALDI-TOF MS confirmed M+ of this compound as 724.15.

Exemplary Synthesis 3

Method of Producing Compound No. D1 by Using Exemplary Compound No. C1 as Intermediate In a 100-ml three-necked flask, 0.72 g (1 mmole) of a compound (C41), 0.71 g (3 mmoles) of a compound (B21) and 50 ml of glycerol were placed and agitated for 5 hours under a nitrogen flow while the system was maintained at a temperature of about 182° C. The reaction product was cooled to room temperature and poured into 200 ml of 0.2N-hydrochloric acid, and a precipitate was collected by filtration, washed with water and dried under a reduced pressure at 100° C. for 5 hours. The precipitate was purified by silica gel chromatography using chloroform as an eluting solution to produce 0.63 g (yield 70%) of an exemplary compound No. D21 as a red-colored powder. MALDI-TOF MS confirmed M+ of this compound as 901.23.

An exemplary compound B1 is substituted for the exemplary compound B21 in exemplary synthesis 1 to synthesize an exemplary compound C1 as an intermediate, and the same reaction as in exemplary synthesis 1 is performed to synthesize an exemplary compound D1.

Exemplary Synthesis 4

Method of Producing Compound No. D4 by Using Exemplary Compound No. C7 as Intermediate An exemplary compound B4 is substituted for the exemplary compound B21 in exemplary synthesis 1 to synthesize an exemplary compound C7 as an intermediate, and the same reaction as in exemplary synthesis 1 is performed to synthesize an exemplary compound D4.

Exemplary Synthesis 5

Method of Producing Compound No. D7 by Using Exemplary Compound No. C5 as Intermediate An exemplary compound B7 is substituted for the exemplary compound B21 in exemplary synthesis 1 to synthesize an exemplary compound C5 as an intermediate, and the same reaction as in exemplary synthesis 1 is performed to synthesize an exemplary compound D7.

Exemplary Synthesis 6

Method of Producing Compound No. D10 by Using Exemplary Compound No. C10 as Intermediate An exemplary compound B10 is substituted for the exemplary compound B21 in exemplary synthesis 1 to synthesize an exemplary compound C10 as an intermediate, and the same reaction as in exemplary synthesis 1 is performed to synthesize an exemplary compound D10.

Exemplary Synthesis 7

Method of Producing Compound No. D15 by Using Exemplary Compound No. C33 as Intermediate An exemplary compound B15 is substituted for the exemplary compound B21 in exemplary synthesis 1 to synthesize an exemplary compound C33 as an intermediate, and the same reaction as in exemplary synthesis 1 is performed to synthesize an exemplary compound D15.

Exemplary Synthesis 8

Method of Producing Compound No. D16 by Using Exemplary Compound No. C33 as Intermediate An exemplary compound B16 is substituted for the exemplary compound B21 in exemplary synthesis 1 to synthesize an exemplary compound C33 as an intermediate, and the same reaction as in exemplary synthesis 1 is performed to produce an exemplary compound D16.

Exemplary Synthesis 9

Method of Producing Compound No. D22 by Using Exemplary Compound No. C43 as Intermediate An exemplary compound B22 is substituted for the exemplary compound B21 in exemplary synthesis 1 to synthesize an exemplary compound C43 as an intermediate, and the same reaction as in exemplary synthesis 1 is performed to synthesize an exemplary compound D22.

Exemplary Synthesis 10

Method of Producing Compound No. D32 by Using Exemplary Compound No. C23 as Intermediate An exemplary compound B32 is substituted for the exemplary compound B21 in exemplary synthesis 1 to synthesize an exemplary compound C23 as an intermediate, and the same reaction as in exemplary synthesis 1 is performed to synthesize an exemplary compound D32.

Exemplary Synthesis 11

Method of Producing Compound No. D37 by Using Exemplary Compound No. C4 as Intermediate An exemplary compound B37 is substituted for the exemplary compound B21 in exemplary synthesis 1 to synthesize an exemplary compound C4 as an intermediate, and the same reaction as in exemplary synthesis 1 is performed to synthesize an exemplary compound D37.

Exemplary Synthesis 12

Method of Producing Compound No. D38 by Using Exemplary Compound No. C27 as Intermediate An exemplary compound B38 is substituted for the exemplary compound B21 in exemplary synthesis 1 to synthesize an exemplary compound C27 as an intermediate, and the same reaction as in exemplary synthesis 1 is performed to synthesize an exemplary compound D38.

Exemplary Synthesis 13

Method of Producing Compound No. D29 by Using Exemplary Compound No. C38 as Intermediate In exemplary synthesis 1, an exemplary compound A17 is substituted for potassium acetate E2 and an exemplary compound B29 is substituted for the exemplary compound B21 to synthesize an exemplary compound C38 as an intermediate, and the same reaction as in exemplary synthesis 1 is performed to synthesize an exemplary compound D29.

Exemplary Synthesis 14

Method of Producing Compound No. D46 by Using Exemplary Compound No. C58 as Intermediate In the exemplary synthesis 1, an exemplary compound B46 was substituted for the exemplary compound B21, and using tetrahydrofuran as a reaction solvent, the reaction was performed under reflux to synthesize an exemplary compound C58 as an intermediate. The exemplary compound C58 is further reacted to synthesize an exemplary compound D46.

Exemplary Synthesis 15

Method of Producing Compound No. D52 by Using Exemplary Compound No. C66 as Intermediate In the exemplary synthesis 1, an exemplary compound B52 was substituted for the exemplary compound B21, and using tetrahydrofuran as a reaction solvent, the reaction was performed under reflux to synthesize an exemplary compound C66 as an intermediate. The exemplary compound C66 is further reacted to synthesize an exemplary compound D52.

Exemplary Synthesis 16

Method of Producing Compound No. D67 by Using Exemplary Compound No. C61 as Intermediate In exemplary synthesis 1, an exemplary compound B67 was substituted for the exemplary compound B21, and all the solvents in the reaction system were changed to tetrahydrofuran, thus the reaction was performed under reflux to synthesize an exemplary compound C61 as an intermediate. The exemplary compound C61 is further reacted to synthesize an exemplary compound D67.

Exemplary Synthesis 17

Method of Producing Compound No. D72 by Using Exemplary Compound No. C73 as Intermediate In exemplary synthesis 1, an exemplary compound B72 was substituted for the exemplary compound B21, and all the solvents in the reaction system were changed to tetrahydrofuran, the reaction was performed under reflux to synthesize an exemplary compound C73 as an intermediate. The exemplary compound C73 is further reacted to synthesize an exemplary compound D72.

Exemplary Synthesis 18

Method of Producing Compound No. D86 by Using Exemplary Compound No. C8 as Intermediate

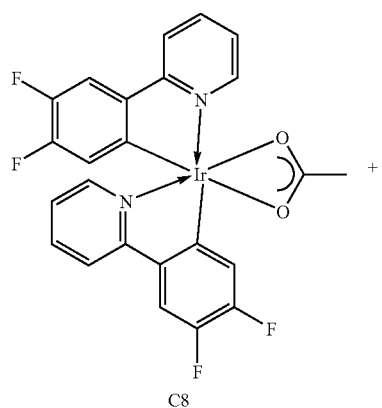

C8

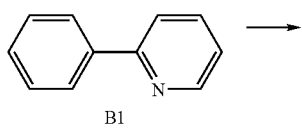

B1

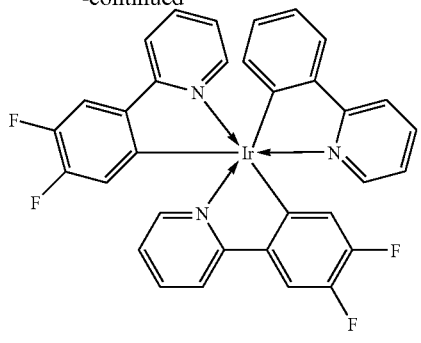

D86

An exemplary compound B9 was substituted for the exemplary compound B21 in exemplary synthesis 1 to synthesize an exemplary compound C8 as an intermediate.

In a 100-ml 3-necked flask, the exemplary compound (C8), the compound (B1) and 50 ml of glycerol were placed and reacted for 5 hours under a nitrogen flow while the system was maintained at about 170° C. to produce an exemplary compound D86.

The present invention utilizes an auxiliary ligand having an unstable 4-membered ring structure as an intermediate, thus enabling a reaction at a low temperature to produce the desired iridium complex at a high yield, and the iridium complex can be used for an organic EL device.

While the present invention has been described with reference to exemplary embodiments it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-099892, filed Mar. 31, 2006, which is hereby incorporated by reference herein in its entirety.

What is claimed is:
1. A method for producing an iridium complex, which comprises
    reacting a metal complex having a partial structure represented by a following general formula (1):

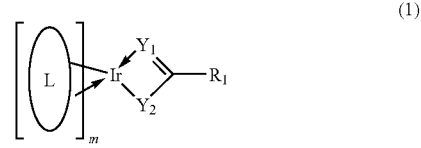

(1)

(wherein L represents a monovalent bidentate ligand having at least one aromatic ring and at least one heterocyclic ring, and the aromatic ring and the heterocyclic ring may each be independently substituted, the aromatic ring being selected from the following structures:

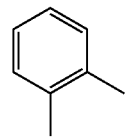

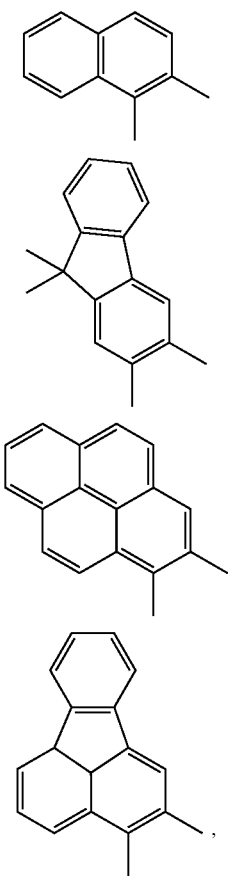

and the heterocyclic ring being selected from the following structures:

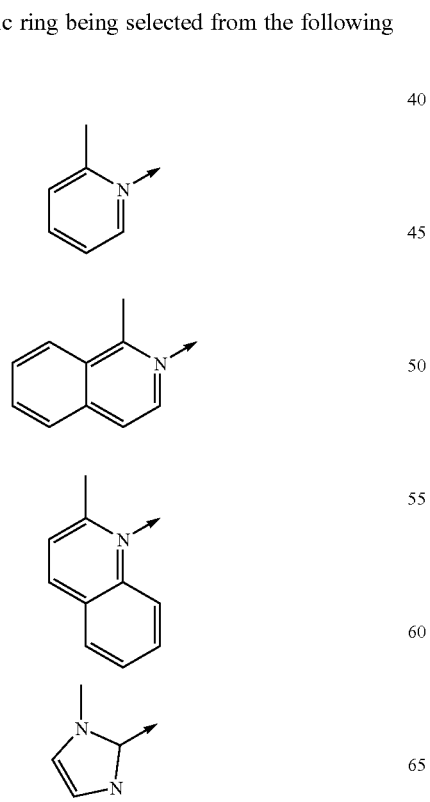

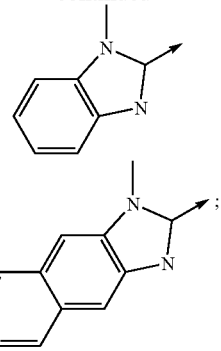

R$_1$ is a group selected from the group consisting of a hydrogen atom, a halogen atom, a linear or branched alkyl group containing 1 to 20 carbon atoms (in which one or unadjacent two or more methylene groups may be replaced by at least one group selected from the group consisting of —O—, —S—, —CO—, —CO—O—, —O—CO—, —CH=CH— and —C≡C—, or one or more methylene groups may be replaced by an arylene group which may be substituted or by a divalent heterocyclic group which may be substituted, and one or two or more hydrogen atoms may be replaced by a fluorine atom, an amino group which may be substituted, a silyl group which may be substituted, a phenyl group which may be substituted, a naphthyl group, a pyrenyl group, a phenanthrenyl group, a chrysenyl group, a fluoranthenyl group, a triphenylenyl group and a heterocyclic group which may be substituted; and Y$_1$ and Y$_2$ are each independently a group selected from an oxygen atom, a sulfur atom, a selenium atom, and a nitrogen atom)

with a compound represented by the following general formula (3):

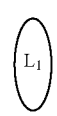

(3)

(wherein L$_1$ is identical to L as described above, thereby producing an iridium complex represented by the following general formula (2):

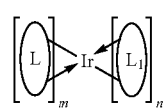

(2)

(wherein m represents an integer from 1 to 3 and n represents an integer from 0 to 2 in which m+n=3).

2. The method of producing an iridium complex according to claim 1, wherein the aromatic ring contained in L in the general formula (1) is a phenyl group which may be substituted, and the heterocyclic ring is an isoquinoline group which may be substituted, and wherein the aromatic ring contained in L$_1$ in the general formula (3) is a phenyl group which may be substituted, and the heterocyclic ring is an isoquinoline group which may be substituted.

3. A method for producing an organic light emission device comprising a first electrode, a second electrode, and an organic compound layer comprising an organic compound, the organic compound layer is disposed between the first and the second electrodes, the method comprising:

forming the first electrode;

forming the organic compound layer which comprises forming the organic compound according to the method for producing an iridium complex of claim 1; and forming the second electrode.

4. A method for producing a display apparatus comprising:

forming a TFT element having a source electrode, a drain electrode, a gate electrode, and a semiconductor layer on a substrate; and the method for producing an organic light emission device according to claim 3, wherein the first electrode is formed so as to be connected to either one of the source electrode and the drain electrode.

* * * * *